US009175057B2

(12) United States Patent
Schlom et al.

(10) Patent No.: US 9,175,057 B2
(45) Date of Patent: *Nov. 3, 2015

(54) IMMUNOGENIC PEPTIDES AND METHODS OF USE

(75) Inventors: Jeffrey Schlom, Potomac, MD (US); Kwong-Yok Tsang, Bethesda, MD (US); Ira H. Pastan, Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 1120 days.

This patent is subject to a terminal disclaimer.

(21) Appl. No.: 13/025,094

(22) Filed: Feb. 10, 2011

(65) Prior Publication Data
US 2011/0165117 A1 Jul. 7, 2011

Related U.S. Application Data

(63) Continuation of application No. 12/280,534, which is a continuation of application No. PCT/US2007/004603, filed on Feb. 21, 2007, now Pat. No. 7,910,692.

(60) Provisional application No. 60/776,506, filed on Feb. 24, 2006.

(51) Int. Cl.
C07K 14/47 (2006.01)
C07K 14/82 (2006.01)
C07H 21/00 (2006.01)
A61K 38/08 (2006.01)
A61K 39/00 (2006.01)

(52) U.S. Cl.
CPC .............. C07K 14/4748 (2013.01); A61K 38/08 (2013.01); A61K 39/0011 (2013.01); C07K 14/82 (2013.01); C12N 2799/023 (2013.01); C12N 2800/00 (2013.01); G01N 2333/70517 (2013.01)

(58) Field of Classification Search
None
See application file for complete search history.

(56) References Cited

U.S. PATENT DOCUMENTS

| | | | |
|---|---|---|---|
| 6,045,802 A | 4/2000 | Schlom et al. | |
| 6,893,869 B2 | 5/2005 | Schlom et al. | |
| 7,399,827 B1 | 7/2008 | Pastan et al. | |
| 7,910,692 B2 * | 3/2011 | Schlom et al. | 530/300 |
| 2004/0019195 A1 | 1/2004 | Scholm et al. | |
| 2004/0171796 A1 | 9/2004 | Schlom et al. | |
| 2005/0054575 A1 | 3/2005 | Schlom et al. | |
| 2005/0186180 A1 | 8/2005 | Schlom et al. | |

FOREIGN PATENT DOCUMENTS

| | | | |
|---|---|---|---|
| WO | WO 00/12706 | 4/2000 | |
| WO | WO 2007/100607 | * 9/2007 | ........... C07K 14/435 |

OTHER PUBLICATIONS

Brinkmann, U. et al., "Novel Genes in the PAGE And GAGE Family of Tumor Antigens Found by Homology Walking in the dbEST Database," Cancer Research 59:1445-1448, Apr. 1, 1999.
Brinkmann, U. et al., "PAGE-1, an X chromosome-linked GAGE-like gene that is expressed in normal and neoplastic prostate, testis, and uterus," Proc. Nat. Acad. Sci. USA 95:10757-10762 (Sep. 1998).
Brown, K. L. and Hancock, R. E.W., "Cationic host defense (antimicrobial) peptides," Current Opinion in Immunology 18:24-30 (2006).
Butt, T. R., et al., "SUMO fusion technology for difficult-to-express proteins," Protein Expression & Purification 43:1-9 (2005).
Celis, "Getting Peptide Vaccines to Work: Just a Matter of Quality Control?," Journal of Clinical Investigation 110(12):1765-1768 (Dec. 2002).
De Smet, K. and Contreras, R., "Human antimicrobial peptides: defensins, cathelicidins and histatins," Biotecnology Letters 27:1337-1347 (Mar. 2005).
Dudley and Rosenberg, "Adoptive-Cell-Transfer Therapy for the Treatment of Patients with Cancer," Nature 3:666-675 (Sep. 2003).
Gura, "Systems for Identifying New Drugs Are Often Faulty," Science 278:1041-1042 (Nov. 7, 1997).
Harlin et al., "Tumor Progression Despite Massive Influx of Activated $CD8_+$ T Cells in a Patient with Malignant Ascites," Cancer Immunol. Immunotherap. 55:1185-1197 (2006).
Iavarone, C. et al., "PAGE4 is a Cytoplasmic Protein that is Expressed in Normal Prostate and in Prostate Cancers," Molecular Cancer Therapeutics 1:329-335 (Mar. 2002).
Janeway et al., "Antigen Recognition by T Cells," Immunobiology 5 www.garlandscience.com (2001).
Kaiser, "First Pass at Cancer Genome Reveals Complex Landscape," Science 313:1370 (Sep. 8, 2006).
Lechleider et al., "Safety and Immunologic Response of a Viral Vaccine to Prostate-Specific Antigen in Combination with Radiation Therapy when Metronomic-Dose Interleukin 2 is Used as an Adjuvant," Clin. Cancer Res. 14(16):5284-5291 (Aug. 15, 2008).
Malakhov, M. et al., "SUMO fusions and SUMO-specific protease for efficient expression and purification of proteins," Journal of Structural and Functional Genomics 5:75-86 (2004).
Marblestone J. et al., "Comparison of SUMO fusion technology with traditional gene fusion systems: Enhanced expression and solubility with SUMO," Protein Sci. 15:1-8 (2005).

(Continued)

Primary Examiner — Peter J Reddig
(74) Attorney, Agent, or Firm — Leydig, Voit & Mayer, Ltd.

(57) ABSTRACT

The PAGE4 gene is expressed in reproductive tissues, and is expressed in reproductive cancers, such as prostate cancer, uterine cancer, and testicular cancer. Immunogenic PAGE4 polypeptides are disclosed herein, as are nucleic acids encoding the immunogenic PAGE4 polypeptides, vectors including these polynucleotides, and host cells transformed with these vectors. These polypeptides, polynucleotides, vectors, and host cells can be used to induce an immune response to PAGE4. Diagnostic methods to detect PAGE4 are also described.

36 Claims, 7 Drawing Sheets

(56) References Cited

OTHER PUBLICATIONS

Marincola et al., "Tumors as Elusive Targets of T-Cell-Based Active Immunotherapy," *Trends in Immunology* 24(6):334-341 (Jun. 2003).

Yokokawa et al., "Identification of cytotoxic T-lymphocyte epitope(s) and its agonist epitope(s) of a novel target for vaccine therapy," *Proceedings of the American Association for Cancer Research Annual Meeting*; 47:530-531 (2006).

Yokokawa et al., "Identification of Cytotoxic T-lymphocyte Epitope(s) and its Agonist Epitope(s) of a Novel Target for Vaccine Therapy (PAGE4)," *Int. J Cancer*. 121:595-605 (2007).

Zhong et al., "Tandem repeat *mhBD2* gene enhance the soluble fusion expression of hBD2 in *Escherichia coli*," *Appl Microbiol Biotechnol* 71:661-667 (2006).

Zuo et al., "Enhanced expression and purification of membrane proteins by SUMO fusion in *Escherichia coli*," *Journal of Structural and Functional Genomics* 6:103-111 (2005).

Zuo et al., "Expression and purification of SARS coronavirus proteins using SUMO-fusions," *Protein Expression and Purification* 42:100-110 (2005).

\* cited by examiner

IMMUNOGENIC PEPTIDES AND METHODS OF USE

CROSS REFERENCE TO RELATED APPLICATIONS

This is a continuation of U.S. patent application Ser. No. 12/280,534, filed Aug. 22, 2008, now U.S. Pat. No. 7,910,692 which is the §371 U.S. National Stage of PCT Application No. PCT/US2007/004603, filed Feb. 21, 2007, which was published in English under PCT Article 21(2), which in turn claims the benefit of U.S. Provisional Application No. 60/776,506, filed Feb. 24, 2006. The prior applications are incorporated herein by reference in their entirety.

FIELD

This application relates to the field of cancer therapeutics, specifically to immunogenic peptides and their use in the treatment of prostate, cervical, uterine and testicular cancer. This application is related to the subject matter of U.S. patent application Ser. No. 09/763,393, which is also incorporated herein by reference.

BACKGROUND

Cancer of the prostate is the most commonly diagnosed cancer in men and is the second most common cause of cancer death (Carter and Coffey, *Prostate* 16:39-48, 1990; Armbruster et al., *Clinical Chemistry* 39:181, 1993). If detected at an early stage, prostate cancer is potentially curable. However, a majority of cases are diagnosed at later stages when metastasis of the primary tumor has already occurred (Wang et al., *Meth. Cancer Res.* 19:179, 1982). Even early diagnosis is problematic because not all individuals who test positive in these screens develop cancer.

Present treatment for prostate cancer includes radical prostatectomy, radiation therapy, or hormonal therapy. With surgical intervention, complete eradication of the tumor is not always achieved and the observed re-occurrence of the cancer (12-68%) is dependent upon the initial clinical tumor stage (Zietman et al., *Cancer* 71:959, 1993). Thus, alternative methods of treatment including prophylaxis or prevention are desirable.

Prostate, testicular, and uterine cancers, are usually treated, in part, by the surgical removal of the affected organ. Up to 30% of the patients in the United States with potentially curable early-stage cancer, such as prostate cancer, will fail standard surgical or radiotherapy in 2004. In addition, patients with metastatic prostate cancer enjoy limited benefit of standard chemotherapy and hormone-based therapies. The metastases may not, however, be susceptible to surgical removal, or they may be too small to be readily detected. Enhancing the patient's immune response to the cancer, and particularly enhancing the response of cytotoxic T lymphocytes ("CTLs") to the cancer, can aid in slowing or stopping the progress of the disease.

Immunotherapy may have great potential to improve these results, combining the tumor specificity of cell-mediated immunity with freedom from toxic chemotherapies.

Immunotherapy involves evoking an immune response against cancer cells based on their production of target antigens. Immunotherapy based on cell-mediated immune responses involves generating a cell-mediated response to cells that produce particular antigenic determinants, while immunotherapy based on humoral immune responses involves generating specific antibodies to cells that produce particular antigenic determinants.

Recent studies show that immunotherapy of cancer patients may be dramatically improved by the finding that $CD8^+$ CTLs recognize and kill tumor cells that display peptides from tumor-associated antigens within MHC Class I molecules. In clinical studies it has been found that effector $CD8^+$ T cells play a major role in tumor regression. Several tumor antigens in prostate cancer models have been identified and HLA allele-specific peptides from those prostate cancer-associated antigens have been identified as $CD8^+$ T cell epitopes. For example, HLA-A2.1 binding peptides were described that were derived from prostate specific antigen (PSA) (Correale et al., *J Immunol* 161:3186, 1998), prostate-specific membrane antigen (PSMA) (Tjoa et al., *Prostate* 28:65, 1996), prostate stem cell antigen (PSCA) (Kiessling et al., *Int J Cancer* 102:390, 2002), and prostate acid phosphatase (Peshwa et al., *Prostate* 36:129, 1998). For PSA, clinical trials are in progress using different vaccine strategies. However, there clearly is a need to identify additional antigens to aid in the diagnosis of a cancer of a reproductive organ, and for use as additional therapeutic agents.

SUMMARY

The PAGE4 gene is expressed in reproductive tissues, and is expressed in reproductive cancers, such as prostate cancer, uterine cancer, cervical cancer and testicular cancer. Immunogenic PAGE4 polypeptides are disclosed herein. These polypeptides can be used in diagnostic assays for PAGE4 expression, as well as for inducing an immune response to PAGE4. Polynucleotides encoding the immunogenic PAGE4 polypeptides, vectors including these polypeptides, host cells transformed with these vectors, and methods of using these polypeptides, polynucleotides, vectors, and host cells are provided herein.

In several embodiments, immunogenic PAGE4 polypeptides are provided, such as an isolated polypeptide including at most ten consecutive amino acids of the amino acid sequence set forth as

```
MSARVRSRSRGRGDGX₁X₂APDVVAFVAPGESQQEEPPTDNQDIEPGQER
EGTPPIEERKX₃X₄GDCQEMDX₅EKTRSERGDGSDVKEX₆X₇PPNPKHX₈
KTKEAGDGQP (SEQ ID NO: 1, PAGE4 CONSENSUS
SHOWING SUBSTITUTIONS)
``` wherein X1 is Q or Y, X2 is E or L, X3 is V or Y, X4 is E or L, X5 is V or L, X6 is K or Y, X7 is T or L, and X8 is A or V. The polypeptide includes one of (a) amino acids 16 to 25 of SEQ ID NO: 1, (b) amino acids 59 to 68 of SEQ ID NO: 1, or (c) amino acids 84 to 92 of SEQ ID NO: 1.

Isolated nucleic acid molecules encoding the immunogenic PAGE4 polypeptides are provided, as well as expression vectors including these nucleic acids. These vectors include viral vectors, such as but not limited to poxviral vectors. Host cells transformed with these vectors are also provided. In one embodiment, a composition is disclosed that includes a first recombinant virus which has incorporated into a viral genome or infectable portion thereof a nucleic acid encoding the immunogenic PAGE4 polypeptide and a second recombinant virus which has incorporated into a viral genome or infectable portion thereof one or more genes or DNA sequences encoding B7-1, B7-2, or B7-1 and B7-2, wherein the composition is able to coinfect a host cell resulting in coexpression of the polypeptide and the B7-1, B7-2, or B7-1 and B7-2 encoding genes or DNA sequences.

Methods of diagnosing a PAGE4-expressing cancer, such as a reproductive cancer are also provided, that include the use of the disclosed immunogenic PAGE4 polypeptides or nucleic acids encoding these polypeptides. Exemplary cancers include prostate, uterine, or testicular cancer.

Methods of inducing an immune response to PAGE4 are also disclosed. The methods include the use of the immunogenic PAGE4 polypeptides disclosed herein, nucleic acids encoded these polypeptides, and/or viral vectors encoding by an immunogenic PAGE4 polypeptide, alone or in conjunction with other agents, such as B7-1, B7-2, and/or a cytokine and/or with traditional cancer therapies, such as surgery, radiation therapy and/or chemotherapy. Methods of treating a subject with a tumor, such as reproductive cancers, for example prostate, uterine, or testicular cancer, are also disclosed.

The foregoing and other features and advantages will become more apparent from the following detailed description of several embodiments, which proceeds with reference to the accompanying figures.

BRIEF DESCRIPTION OF THE FIGURES

FIG. 1B presents a comparison of the stability of HLA-A2 peptide complexes of PAGE4 native and agonist peptides. T2 cells were incubated overnight with P16 peptide (○), P16-1 (•), P16-2 (▲), P84 (□) and P84-1 (■) peptides at a concentration of 12.5 µg/ml and then were washed free of unbound peptide and incubated with brefeldin A to block delivery of new class 1 molecules to the cell surface. At the indicated times, cells were stained for the presence of surface peptide-HLA-A2 complexes. Results are expressed in relative percentage of binding compared with 100% at time 0.

SEQUENCE LISTING

Figure 1:
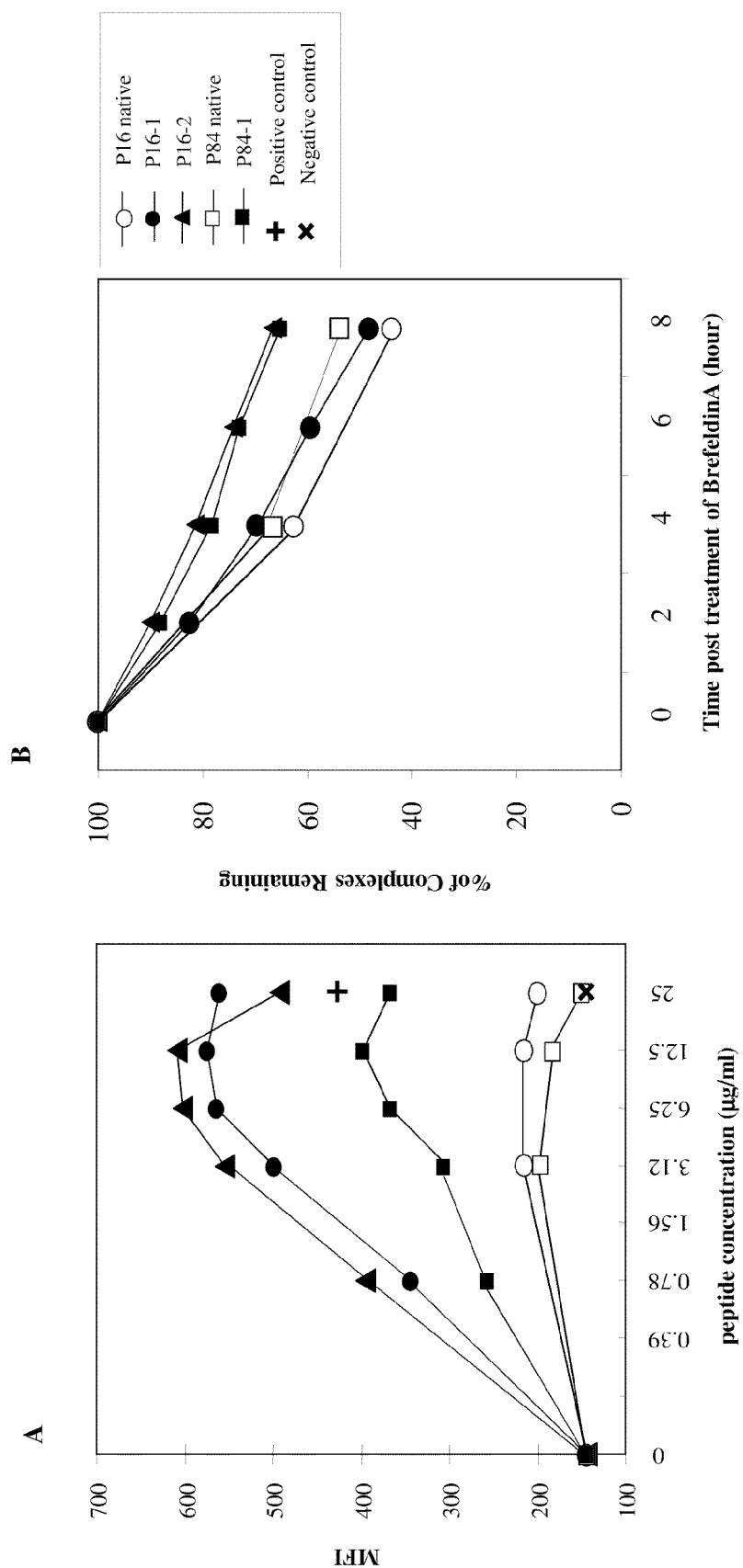
FIGS. 1A and 1B are line graphs showing the binding of native PAGE4 peptides and their agonist peptides to HLA-A2 molecules. Peptides were analyzed for binding to T2 cell line as described in Example 1. For the results presented in FIG. 1A, peptides were used at concentrations of 0 to 25 µg/ml. P16 peptide (○), P16-1 (•), P16-2 (▲), P84 (□) and P84-1 (■), positive control (MUC-1 peptide) (+) and negative control (HLA-A3 binding peptide) (X). Results are expressed in mean fluorescence intensity (MFI).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [4239-73266-18, Feb. 10, 2011, 4.40 KB], which is incorporated by reference herein. In the accompanying sequence listing:

SEQ ID NO: 1 is a consensus amino acid sequence for PAGE4

SEQ ID NO: 2 is an exemplary wild-type PAGE4 amino acid sequence.

SEQ ID NO: 3 is a nucleic acid sequence encoding a wild-type PAGE4 amino acid sequence.

SEQ ID NOs: 4 and 5 are primer sequences.

DETAILED DESCRIPTION

I. Abbreviations

APC: antigen presenting cell
CTL: cytotoxic T lymphocyte
DC: dendritic cell
DMSO: dimethyl sulfoxide
E/T: effector to target
FACS: fluorescence activated cell sorter
FITC: fluorescein isothiocyanate
G-CSF: granulocyte colony stimulating factor
GM-CSF: granulocyte/macrophage colony stimulating factor
HLA: human major histocompatibility complex
ICAM: intracellular adhesion molecule
IL: interleukin
IFN: interferon
LFA: leukocyte function associated antigen
MHC: Major Histocompatibility Complex
PBL: peripheral blood lymphocytes
PBMC: peripheral blood mononuclear cells
PE: phycoerythrin
RANTES: Regulated on Activation, Normal T Expressed and Secreted
TCR: T cell receptor
TNF: tumor necrosis factor
TIL: tumor infiltrating lymphocytes
µM: micromolar

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Adjuvant: A vehicle used to enhance antigenicity. Adjuvants include a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunstimulatory oligonucleotides (such as those including a CpG motif) can also be used as adjuvants (for example see U.S. Pat. Nos. 6,194,388; 6,207,646; 6,214,806; 6,218,371; 6,239,116; 6,339,06; 6,406,705; and 6,429,199). Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L and 41 BBL Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and 2-dimensional nuclear magnetic resonance.

An antigen can be a tissue-specific antigen, or a disease-specific antigen. These terms are not exclusive, as a tissue-specific antigen can also be a disease specific antigen. A tissue-specific antigen is expressed in a limited number of tissues, such as a single tissue. Specific, non-limiting examples of a tissue specific antigen are a prostate specific antigen, a uterine specific antigen, and/or a testes specific antigen. A tissue specific antigen may be expressed by more than one tissue, such as, but not limited to, an antigen that is expressed in more than one reproductive tissue, such as in both prostate and uterine tissue. A disease-specific antigen is expressed coincidentally with a disease process. Specific non-limiting examples of a disease-specific antigen are an antigen whose expression correlates with, or is predictive of, tumor formation, such as prostate cancer and/or uterine cancer and/or testicular cancer. A disease-specific antigen can be an antigen recognized by T cells or B cells.

Amplification: Of a nucleic acid molecule (e.g., a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Antibody: Immunoglobulin molecules and immunologically active portions of immunoglobulin molecules, i.e., molecules that contain an antigen binding site that specifically binds (immunoreacts with) an antigen.

A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the $V_L$, $V_H$, $C_L$ and $C_{H1}$ domains; (ii) an $F_d$ fragment consisting of the $V_H$ and $C_{H1}$ domains; (iii) an Fv fragment consisting of the VL and VH domains of a single arm of an antibody, (iv) a dAb fragment (Ward et al., *Nature* 341:544-546, 1989) which consists of a $V_H$ domain; (v) an isolated complementarity determining region (CDR); and (vi) a F(ab')$_2$ fragment, a bivalent fragment comprising two Fab fragments linked by a disulfide bridge at the hinge region.

Immunoglobulins and certain variants thereof are known and many have been prepared in recombinant cell culture (e.g., see U.S. Pat. Nos. 4,745,055; 4,444,487; WO 88/03565; EP 256,654; EP 120,694; EP 125,023; Faoulkner et al., *Nature* 298:286, 1982; Morrison, *J. Immunol.* 123:793, 1979; Morrison et al., *Ann Rev. Immunol* 2:239, 1984).

Animal: Living multi-cellular vertebrate organisms, a category that includes, for example, mammals and birds. The term mammal includes both human and non-human mammals. Similarly, the term "subject" includes both human and veterinary subjects.

Cancer or Tumor: A malignant neoplasm that has undergone characteristic anaplasia with loss of differentiation, increase rate of growth, invasion of surrounding tissue, and is capable of metastasis. A reproductive cancer is a cancer that has its primary origin in a reproductive tissue, such as in the uterus, testes, ovary, prostate, fallopian tube, or penis. For example, prostate cancer is a malignant neoplasm that arises in or from prostate tissue, and uterine cancer is a malignant neoplasm that arises in or from uterine tissue, and testicular cancer is a malignant neoplasm that arises in the testes. Residual cancer is cancer that remains in a subject after any form of treatment given to the subject to reduce or eradicate thyroid cancer. Metastatic cancer is a cancer at one or more sites in the body other than the site of origin of the original (primary) cancer from which the metastatic cancer is derived. Prostate cancer is a malignant tumor, generally of glandular origin, of the prostate. Prostate cancers include adenocarcinomas and small cell carcinomas. Many prostate cancers express prostate specific antigen (PSA).

cDNA (complementary DNA): A piece of DNA lacking internal, non-coding segments (introns) and regulatory sequences that determine transcription. cDNA is synthesized in the laboratory by reverse transcription from messenger RNA extracted from cells.

Conservative variants: "Conservative" amino acid substitutions are those substitutions that do not substantially affect or decrease an activity or antigenicity of an antigenic epitope of PAGE4. Specific, non-limiting examples of a conservative substitution include the following examples:

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the substituted polypeptide also immunoreact with the unsubstituted polypeptide. Non-conservative substitutions are those that reduce an activity or antigenicity.

CD4: Cluster of differentiation factor 4, a T cell surface protein that mediates interaction with the MHC Class II molecule. CD4 also serves as the primary receptor site for HIV on T cells during HIV infection. Cells that express CD4 are often helper T cells.

CD8: Cluster of differentiation factor 8, a T cell surface protein that mediates interaction with the MHC Class I molecule. Cells that express CD8 are often cytotoxic T cells.

Chemotherapy; chemotherapeutic agents: As used herein, any chemical agent with therapeutic usefulness in the treatment of diseases characterized by abnormal cell growth. Such diseases include tumors, neoplasms and cancer as well as diseases characterized by hyperplastic growth such as psoriasis. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g. see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). The immunogenic PAGE4 polypeptides disclosed herein can be used in conjunction with additional chemotherapeutic agents.

Costimulatory molecule: Although engagement of the TCR with peptide-MHC delivers one signal to the T cell that, this signal alone can be insufficient to activate the T cell. Costimulatory molecules are molecules that, when bound to their ligand, deliver a second signal required for the T cell to become activated. The most well-known costimulatory molecule on the T cell is CD28, which binds to either B7-1 (also called CD80) or B7-2 (also known as CD86). An additional costimulatory molecule is B7-3. Accessory molecules that also provide a second signal for the activation of T cells include intracellular adhesion molecule (ICAM-1 and ICAM-2), leukocyte function associated antigen (LFA-1, LFA-2 and LFA-3). Integrins and tumor necrosis factor (TNF) superfamily members can also serve as co-stimulatory molecules.

Degenerate variant: A polynucleotide encoding an epitope of PAGE4 that includes a sequence that is degenerate as a result of the genetic code. There are 20 natural amino acids, most of which are specified by more than one codon. Therefore, all degenerate nucleotide sequences are included in this disclosure as long as the amino acid sequence of the PAGE4 polypeptide encoded by the nucleotide sequence is unchanged.

Dendritic cell (DC): Dendritic cells are the principle antigen presenting cells (APCs) involved in primary immune responses. Dendritic cells include plasmacytoid dendritic cells and myeloid dendritic cells. Their major function is to obtain antigen in tissues, migrate to lymphoid organs and present the antigen in order to activate T cells. Immature dendritic cells originate in the bone marrow and reside in the periphery as immature cells.

Diagnostic: Identifying the presence or nature of a pathologic condition, such as, but not limited to, a reproductive cancer, such as prostate, uterine or testicular cancer. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (for example, severity) of a pathologic condition, such as prostate cancer, or metastasis.

Epitope: An antigenic determinant. These are particular chemical groups or peptide sequences on a molecule that are antigenic (that elicit a specific immune response). An antibody specifically binds a particular antigenic epitope on a polypeptide. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or 8 to 10 amino acids in a unique spatial conformation. Methods of determining spatial conformation of epitopes include, for example, x-ray crystallography and 2-dimensional nuclear magnetic resonance. See, e.g., "Epitope Mapping Protocols" in *Methods in Molecular Biology*, Vol. 66, Glenn E. Morris, Ed (1996). In one embodiment, an epitope binds an MHC molecule, such an HLA molecule or a DR molecule. These molecules bind polypeptides having the correct anchor amino acids separated by about eight to about ten amino acids, such as nine amino acids.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like can be used. In one embodiment, when cloning in mammalian cell systems, promoters derived from the genome of mammalian cells (such as the metallothionein promoter) or from mammalian viruses (such as the retrovirus long terminal repeat; the adenovirus late promoter; the vaccinia virus 7.5K promoter) can be used. Promoters produced by recombinant DNA or synthetic techniques can also be used to provide for transcription of the nucleic acid sequences.

Heterologous: Originating from separate genetic sources or species. A polypeptide that is heterologous to PAGE4 originates from a nucleic acid that does not encode PAGE4. In one specific, non-limiting example, a polypeptide comprising nine consecutive amino acids from PAGE4 and a heterologous amino acid sequence includes a β-galactosidase, a maltose binding protein, and albumin, hepatitis B surface antigen, or an immunoglobulin amino acid sequence. Generally, an antibody that specifically binds to a protein of interest will not specifically bind to a heterologous protein.

Host cells: Cells in which a vector can be propagated and its DNA expressed. The cell may be prokaryotic or eukaryotic. The cell can be mammalian, such as a human cell. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunogenic peptide: A peptide which comprises an allele-specific motif or other sequence such that the peptide will bind an MHC molecule and induce a cytotoxic T lymphocyte ("CTL") response, or a B cell response (e.g. antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide.

Immunogenic peptides can also be identified by measuring their binding to a specific MHC protein (e.g. HLA-A02.01) and by their ability to stimulate CD4 and/or CD8 when presented in the context of the MHC protein.

In one example, an immunogenic "PAGE-4 peptide" is a series of contiguous amino acid residues from the PAGE-4 protein generally between 7 and 20 amino acids in length, such as about 8 to 11 residues in length. Immunogenic PAGE4 polypeptides, are disclosed, for example, in PCT Publication No. 00/12706, which is incorporated herein by reference. Specific immunogenic PAGE4 polypeptides are disclosed herein that are 9 or 10 amino acid residues in length. Generally, immunogenic PAGE4 polypeptide can be used to induce an immune response in a subject, such as a B cell response or a T cell response. In one example, an immunogenic PAGE4 polypeptide, when bound to a Major Histocompatibility Complex Class I molecule, activates cytotoxic T lymphocytes (CTLs) against cells expressing wild-type PAGE-4 protein. Induction of CTLs using synthetic peptides and CTL cytotoxicity assays known in the art, see U.S. Pat. No. 5,662,907, which is incorporated herein by reference. In one example, an immunogenic peptide includes an allele-specific motif or other sequence such that the peptide will bind an MHC molecule and induce a cytotoxic T lymphocyte ("CTL") response against the antigen from which the immunogenic peptide is derived.

Immunogenic composition: A composition comprising an immunogenic PAGE4 polypeptide or a nucleic acid encoding the immunogenic PAGE4 polypeptide that induces a measurable CTL response against cells expressing PAGE4 polypeptide, or induces a measurable B cell response (such as production of antibodies that specifically bind PAGE4) against a PAGE4 polypeptide. For in vitro use, the immunogenic composition can consist of the isolated nucleic acid, vector including the nucleic acid/or immunogenic peptide. For in vivo use, the immunogenic composition will typically comprise the nucleic acid, vector including the nucleic acid, and or immunogenic polypeptide, in pharmaceutically acceptable carriers, and/or other agents. An immunogenic composition can optionally include an adjuvant, a costimulatory molecule, or a nucleic acid encoding a costimulatory molecule. A PAGE4 polypeptide, or nucleic acid encoding the polypeptide, can be readily tested for its ability to induce a CTL by art-recognized assays.

Inhibiting or treating a disease: Inhibiting a disease, such as tumor growth, refers to inhibiting the full development of a disease. In several examples, inhibiting a disease refers to lessening symptoms of a tumor, such as preventing the development of paraneoplastic syndrome in a person who is known to have a reproductive cancer, such as prostate, uterine or testicular cancer, or lessening a sign or symptom of the tumor. "Treatment" refers to a therapeutic intervention that ameliorates a sign or symptom of a disease or pathological condition related to the disease, such as the tumor.

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule to facilitate detection of that molecule. Specific, non-limiting examples of labels include fluorescent tags, enzymatic linkages, and radioactive isotopes.

Linker sequence: A linker sequence is an amino acid sequence that covalently links two polypeptide domains. Linker sequences can be included in the between the PAGE4 epitopes disclosed herein to provide rotational freedom to the linked polypeptide domains and thereby to promote proper domain folding and presentation to the MHC. By way of example, in a recombinant polypeptide comprising two PAGE4 domains, linker sequences can be provided between them, such as a polypeptide comprising PAGE4 polypeptide-linker-PAGE4 polypeptide. Linker sequences, which are generally between 2 and 25 amino acids in length, are well known in the art and include, but are not limited to, the glycine(4)-serine spacer (GGGGSx3) described by Chaudhary et al., Nature 339:394-397, 1989.

Lymphocytes: A type of white blood cell that is involved in the immune defenses of the body. There are two main types of lymphocytes: B cells and T cells.

Major Histocompatibility Complex (MHC): A generic designation meant to encompass the histocompatibility antigen systems described in different species, including the human leukocyte antigens ("HLA").

Mammal: This term includes both human and non-human mammals. Similarly, the term "subject" includes both human and veterinary subjects.

Neoplasm: An abnormal cellular proliferation, which includes benign and malignant tumors, as well as other proliferative disorders.

Oligonucleotide: A linear polynucleotide sequence of up to about 100 nucleotide bases in length.

Open reading frame (ORF): A series of nucleotide triplets (codons) coding for amino acids without any internal termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence, such as a sequence that encodes a PAGE4 polypeptide. Generally, operably linked DNA sequences are contiguous and, where necessary to join two protein-coding regions, in the same reading frame.

PAGE4: A polypeptide expressed in prostate and other tissues. In particular, it is expressed in cancers of the prostate, ovaries, and testicles. An exemplary sequence of the PAGE-4 is set forth in the detailed description below, and is described in PCT Publication No. WO 00/12706, which is incorporated by reference herein. As used herein, a "PAGE-4 protein" refers to the protein encoded by the PAGE-4 gene. With respect to immunogenic compositions comprising a PAGE-4 protein, it further refers to variations of this protein in which there are conservative substitutions of one or more amino acids of the protein, or deletions or insertions of one or more amino acids, so long as the variations do not alter by more than 20% the ability of the protein, when bound to a Major Histocompatibility Complex class I molecule, to activate cytotoxic T lymphocytes against cells expressing wild-type PAGE-4 protein. Wild-type PAGE4 (for example, SEQ ID NO: 1) is expressed by uterine, prostate and testicular cancers (see Brinkman et al., Cancer Res. 59: 1445-1448, 1999; Brinkman et al., PNAS USA 95: 10757-19762, 1998).

Peptide Modifications: PAGE4 epitopes include synthetic embodiments of peptides described herein. In addition, analogs (non-peptide organic molecules), derivatives (chemically functionalized peptide molecules obtained starting with the disclosed peptide sequences) and variants (homologs) of these proteins can be utilized in the methods described herein. Each polypeptide of this disclosure is comprised of a sequence of amino acids, which may be either L- and/or D-amino acids, naturally occurring and otherwise.

Peptides can be modified by a variety of chemical techniques to produce derivatives having essentially the same activity as the unmodified peptides, and optionally having other desirable properties. For example, carboxylic acid groups of the protein, whether carboxyl-terminal or side chain, can be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of an immunogenic PAGE4 polypeptide having measurable or enhanced ability to generate an immune response. For computer modeling applications, a pharmacophore is an idealized three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs," in Klegerman & Groves, eds., 1993, *Pharmaceutical Biotechnology*, Interpharm Press: Buffalo Grove, Ill., pp. 165-174 and *Principles of Pharmacology*, Munson (ed.) 1995, Ch. 102, for descriptions of techniques used in CADD. Also included are mimetics prepared using such techniques.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

A "therapeutically effective amount" is a quantity of a composition or a cell to achieve a desired effect in a subject being treated. For instance, this can be the amount necessary to induce an immune response, inhibit tumor growth or to measurably alter outward symptoms of the tumor. When administered to a subject, a dosage will generally be used that will achieve target tissue concentrations (for example, in lymphocytes) that has been shown to achieve an in vitro effect.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Polypeptide: Any chain of amino acids, regardless of length or post-translational modification (e.g., glycosylation or phosphorylation). In one embodiment, the polypeptide is a PAGE4 polypeptide. A polypeptide can be between 3 and 30 amino acids in length. In one embodiment, a polypeptide is from about 7 to about 25 amino acids in length. In yet another embodiment, a polypeptide is from about 8 to about 10 amino acids in length. In yet another embodiment, a peptide is about 9 amino acids in length. With regard to polypeptides, "comprises" indicates that additional amino acid sequence or other molecules can be included in the molecule, "consists essentially of" indicates that additional amino acid sequences are not included in the molecule, but that other agents (such as labels or chemical compounds) can be included, and "consists of" indicates that additional amino acid sequences and additional agents are not included in the molecule.

Probes and primers: A probe comprises an isolated nucleic acid attached to a detectable label or reporter molecule. Primers are short nucleic acids, preferably DNA oligonucleotides, of about 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, for example by polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers can be selected that comprise about 20, 25, 30, 35, 40, 50 or more consecutive nucleotides.

Purified: The epitopes of PAGE4 disclosed herein can be purified (and/or synthesized) by any of the means known in the art (see, e.g., *Guide to Protein Purification*, ed. Deutscher, *Meth. Enzymol.* 185, Academic Press, San Diego, 1990; and Scopes, *Protein Purification: Principles and Practice*, Springer Verlag, New York, 1982). Substantial purification denotes purification from other proteins or cellular components. A substantially purified protein is at least about 60%, 70%, 80%, 90%, 95%, 98% or 99% pure. Thus, in one specific, non-limiting example, a substantially purified protein is 90% free of other proteins or cellular components. Thus, the term purified does not require absolute purity; rather, it is intended as a relative term. For example, a purified nucleic acid is one in which the nucleic acid is more enriched than the nucleic acid in its natural environment within a cell. In additional embodiments, a nucleic acid or cell preparation is purified such that the nucleic acid or cell represents at least about 60% (such as, but not limited to, 70%, 80%, 90%, 95%, 98% or 99%) of the total nucleic acid or cell content of the preparation, respectively.

RANTES (CCL5): A cytokine that is a member of the interleukin-8 superfamily of cytokines. RANTES is believed to be a selective attractant for memory T lymphocytes and monocytes. RANTES binds to CCR5 (a coreceptor of HIV).

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Selectively hybridize: Hybridization under moderately or highly stringent conditions that excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA versus DNA) of the hybridizing regions of the nucleic acids can be considered in selecting hybridization conditions. An additional consideration is whether one of the nucleic acids is immobilized, for example, on a filter.

A specific example of progressively higher stringency conditions is as follows: 2×SSC/0.1% SDS at about room temperature (hybridization conditions); 0.2×SSC/0.1% SDS at about room temperature (low stringency conditions); 0.2× SSC/0.1% SDS at about 42° C. (moderate stringency conditions); and 0.1×SSC at about 68° C. (high stringency conditions). One of skill in the art can readily determine variations on these conditions (e.g., *Molecular Cloning: A Laboratory Manual*, 2nd ed., vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a PAGE4 polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a PAGE4 polypeptide are typically characterized by possession of at least 75%, for example at least 80%, sequence identity counted over the full length alignment with the amino acid sequence of PAGE4 using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and can possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specific binding agent: An agent that binds substantially only to a defined target. Thus a PAGE4 specific binding agent is an agent that binds substantially to a PAGE4 polypeptide. In one embodiment, the specific binding agent is a monoclonal or polyclonal antibody that specifically binds PAGE4.

T Cell: A white blood cell critical to the immune response. T cells include, but are not limited to, CD4$^+$ T cells and CD8$^+$ T cells. A CD4$^+$ T lymphocyte is an immune cell that carries a marker on its surface known as "cluster of differentiation 4" (CD4). These cells, also known as helper T cells, help orchestrate the immune response, including antibody responses as well as killer T cell responses. CD8$^+$ T cells carry the "cluster of differentiation 8" (CD8) marker. In one embodiment, a CD8 T cell is a cytotoxic T lymphocyte. In another embodiment, a CD8 cell is a suppressor T cell.

Therapeutically active polypeptide: An agent, such as an epitope of PAGE4 that causes induction of an immune response, as measured by clinical response (for example increase in a population of immune cells, increased cytolytic activity against cells that express PAGE4, or measurable reduction of tumor burden). Therapeutically active molecules can also be made from nucleic acids. Examples of a nucleic acid based therapeutically active molecule is a nucleic acid sequence that encodes a PAGE4 epitope, wherein the nucleic acid sequence is operably linked to a control element such as a promoter.

In one embodiment, a therapeutically effective amount of an epitope of PAGE4 is an amount used to generate an immune response, or to treat prostate cancer or breast cancer in a subject. Treatment refers to a therapeutic intervention that ameliorates a sign or symptom of a reproductive cancer, or a reduction in tumor burden.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art. Vectors include plasmid vectors, including plasmids for expression in gram negative and gram positive bacterial cell. Exemplary vectors include those for expression in *E. coli* and *Salmonella*. Vectors also include viral vectors, such as, but are not limited to, retrovirus, orthopox, avipox, fowlpox, capripox, suipox, adenoviral, herpes virus, alpha virus, baculovirus, Sindbis virus, vaccinia virus and poliovirus vectors.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Immunogenic PAGE4 Peptides

PAGE4 is a polypeptide which is transcribed in prostate cells, in prostate cancer cells, in the cervix and in many uterine cancers. PAGE4 is disclosed in published PCT Application No. WO 00/12706, published Mar. 9, 2000 (Pastan et al.), which is incorporated herein by reference.

In one embodiment, the polypeptide has a sequence set forth as:

(SEQ ID NO: 1)
MSARVRSRSRGRGDGX$_1$X$_2$APDVVAFVAPGESQQEEPPTDNQDIE

PGQEREGTPPIEERKX$_3$X$_4$GDCQEMDX$_5$EKTRSERGDGSDVKEX$_6$X$_7$PPN

PKHX$_8$KTKEAGDGQP

An exemplary amino acid sequence is set forth in published PCT Application No. WO 00/12706, as: MSARVRSRSR-GRGDGQEAPDVVAFVAPGESQQEEPPTD-NQDIEPGQEREGT PPIEERKVEGDCQEMDLEK-TRSERGDGSDVKEKTPPNPKHAKTKEAGDGQP (SEQ ID NO: 2); see also GENBANK Accession No. AF275258, incorporated herein by reference.

In other embodiments, PAGE4 has an amino acid sequence least 90% identical to SEQ ID NO: 2, for example a polypeptide that has about 91%, 92%, 93%, 94%, 95%, 96%, 97%, 98% or even higher sequence identity to SEQ ID NO: 2. Additional variants have been described (see below and see published PCT Application No. WO 00/12709, herein incorporated by reference, for a complete description of these polypeptides. See also GENBANK Accession No. AF275258, incorporated herein by reference).

Using the genetic code, one of skill in the art can readily produce a nucleic acid sequence encoding PAGE4. In one example, PAGE4 is encoded by a nucleic acid having a sequence set forth as:

(SEQ ID NO: 3)
ggtcgacctt cgccaggctc tctgctgact caagttcttc agttcacgat cttctagttg cagcgatgag tgcacgagtg agatcaagat ccagaggaag aggagatggt caggaggctc ccgatgtggt tgcattcgtg gctcccggtg aatctcagca agaggaacca ccaactgaca atcaggatat tgaacctgga caagagagag aaggaacacc tccgatcgaa gaacgtaaag tagaaggtga ttgccaggaa atggatctgg aaaagactcg gagtgagcgt ggagatggct ctgatgtaaa agagaagact ccacctaatc ctaagcatgc taagactaaa gaagcaggag atgggcagcc ataagttaaa aagaagacaa gctgaagcta cacacatggc tgatgtcaca ttggaaatgt gactgaaaat ttggaaattc tctcaataga gtctgagttt tctctgaaga aaaaaaaaaa a, (see also PCT Publication No. WO 00/12709 (Pastan et al.), and GENBANK Accession No. AF277258, which are both incorporated herein by reference).

Immunogenic fragments of PAGE4 (and PAGE4 itself), can be chemically synthesized by standard methods. If desired, polypeptides can also be chemically synthesized by emerging technologies. One such process is described in W. Lu et al., *Federation of European Biochemical Societies Letters*. 429:31-35, 1998. Polypeptides can also be produced using molecular genetic techniques, such as by inserting a nucleic acid encoding PAGE4 or an epitope thereof into an expression vector, introducing the expression vector into a host cell, and isolating the polypeptide (see below).

Immunogenic PAGE4 polypeptides are disclosed herein. These peptides comprise at most ten amino acids, such as nine consecutive amino acids of a PAGE4 polypeptide, such as a polypeptide having the amino acid sequence set forth as:

MSARVRSRSRGRGDGX$_1$X$_2$APDVVAFVAPGESQQEEPPTDNQDIE

PGQEREGTPPIEERKX$_3$X$_4$GDCQEMDX$_5$EKTRSERGDGSDVKEX$_6$X$_7$PPN

PKHX$_8$KTKEAGDGQP (SEQ ID NO: 1, PAGE4 CONSENSUS

SHOWING SUBSTITUTIONS)

wherein X1 is Q or Y, X2 is E or L, X3 is V or Y, X4 is E or L, X5 is V or L, X6 is K or Y, X7 is T or L, and X8 is A or V In several embodiments, the PAGE4 polypeptide comprises at nine amino acids of SEQ ID NO: 1. Thus, the polypeptide comprises one of (a) amino acids 16 to 25 of SEQ ID NO: 1, (b) amino acids 59 to 68 of SEQ ID NO: 1, or (c) amino acids 84 to 92 of SEQ ID NO: 1 and does not include additional consecutive amino acids from the sequence set forth as SEQ ID NO: 1.

The immunogenic PAGE4 polypeptides disclosed herein do not include all the additional consecutive amino acids of SEQ ID NO: 1. In one embodiment, the polypeptide does not include amino acids 1-15 of SEQ ID NO: 1.

Without being bound by theory, it is believed that the presentation of peptides by MHC Class I molecules involves binding to the cleft in an MHC Class I molecule through the anchor residues of the peptide and ultimate presentation on the cell surface. Depending upon the particular anchor residues, among other things, certain peptides can bind more tightly to particular HLA molecules than others. Peptides that bind well are usually "dominant" epitopes, while those that bind less well are often "subdominant" or "cryptic" epitopes. Dominant epitopes of either self proteins or foreign proteins evoke strong tolerance or immune responses. Subdominant or cryptic epitopes generate weak responses or no responses at all. Without being bound by theory, tighter binding by dominant epitopes to HLA molecules results in their denser presentation on the cell surface, greater opportunity to react with immune cells and greater likelihood of eliciting an immune response or tolerance. MHC Class I molecules present epitopes from endogenous proteins for presentation to CTL cells. HLA A, HLA B and HLA C molecules bind peptides of about eight to ten amino acids in length (such as nine amino acids in length) that have particular anchoring residues. The anchoring residues recognized by an HLA Class I molecule depend upon the particular allelic form of the HLA molecule. A CD8+ T cell bears T cell receptors that recognize a specific epitope when presented by a particular HLA molecule on a cell. When a CTL precursor that has been stimulated by an antigen presenting cell to become a cytotoxic T lymphocyte contacts a cell that bears such an HLA-peptide complex, the CTL forms a conjugate with the cell and destroys it. In several examples presented herein, the polypeptides that are disclosed bind and are presented by HLA-A2.1.

In several examples, the immunogenic PAGE4 polypeptide can be repeated, such that the polypeptide includes several copies of the immunogenic PAGE4 polypeptide. However, only one copy of the immunogenic PAGE4 polypeptide can be included in the immunogenic peptide.

In one embodiment, an immunogenic PAGE4 polypeptide includes, consists essentially of, or consists of amino acids 16 to 25 of SEQ ID NO: 1. For example, the immunogenic PAGE4 polypeptide can include, consist essentially or of consist of amino acids 16 to 25 of SEQ ID NO: 1, wherein amino acid 1 ($X_1$) is a glutamine and amino acid 2 ($X_2$) is a glutamic acid (P16 and 16-1). The immunogenic PAGE4 polypeptide can include, consist essentially or of consist of amino acids 16 to 25 of SEQ ID NO: 1, wherein amino acid 1 ($X_1$) is a glutamine and amino acid 2 ($X_2$) is a leucine (P16-1). The immunogenic PAGE4 polypeptide can include, consist essentially or of consist of amino acids 16 to 25 of SEQ ID NO: 1, wherein amino acid 1 ($X_1$) is a tyrosine and amino acid 2 ($X_2$) is a leucine (P16-2). In several examples, two, three, four, five copies of the immunogenic PAGE4 polypeptide are include in an immunogenic molecule. The copies of the immunogenic PAGE4 polypeptide can be separated by peptide linkers.

In another embodiment, the immunogenic PAGE4 polypeptide includes, consists essentially of, or consists of amino acids 59-68 of SEQ ID NO: 1 (P59). For example, the immunogenic PAGE4 polypeptide can include, consist essentially of, or consist of amino acids 59-68 of SEQ ID NO: 1, wherein amino acid 1 ($X_3$) is a valine amino acid 2 ($X_4$) is a leucine (P-59-1). The immunogenic PAGE4 polypeptide can include, consist essentially of, or consist of amino acids 59-68 of SEQ ID NO: 1, wherein amino acid 1 ($X_3$) is a tyrosine, amino acid 2($X_4$) is a leucine, and amino acid 3 ($X_5$) is a valine.

In a further embodiment, the immunogenic PAGE4 polypeptide can include, consist essentially of, or consist of amino acids 84-92 of SEQ ID NO: 1. For example, the immunogenic PAGE4 polypeptide can include, consist essentially of, or consist of amino acids 84-92 of SEQ ID NO: 1, wherein amino acid 1 ($X_6$) is a tyrosine, amino acid 2 ($X_7$) is a leucine and amino acid 9 ($X_8$) is a valine.

In additional examples, the polypeptide can be a fusion protein and can also include heterologous sequences to PAGE4 (such as amino acid sequences of at least nine amino acids in length that are not included in SEQ ID NO: 1). Thus, in several specific non-limiting examples, the immunogenic peptide is a fusion polypeptide, for example the polypeptide includes six sequential histidine residues, a β-galactosidase amino acid sequence, or an immunoglobulin amino acid sequence. The polypeptide can also be covalently linked to a carrier. Suitable carriers include, but are not limited to, a hepatitis B small envelope protein HBsAg). This protein has the capacity to self assemble into aggregates and can form viral-like particles. The preparation of HBsAg is well documented, see for example European Patent Application Publication No. EP-A-0 226 846, European Patent Application Publication No. EP-A-0 299 108 and PCT Publication No. WO 01/117554, and the amino acid sequence disclosed, for example, in Tiollais et al., Nature, 317: 489, 1985, and European Patent Publication No. EP-A-0 278 940, and PCT Publication No. WO 91/14703, all of which are incorporated herein by reference.

As noted above, the polypeptide can optionally include repetitions of one of more of the immunogenic PAGE4 polypeptides disclosed herein. In one specific, non-limiting example, the polypeptide includes two, three, four, five, or up to ten repetitions of one of the immunogenic PAGE4 polypeptides. In additional examples, the polypeptide includes two, three, four, five or up to ten repetitions of two or three of immunogenic PAGE4 polypeptides disclosed herein. A linker sequence can optionally be included between the immunogenic PAGE4 polypeptides. In all of these examples, the polypeptide does not include the full-length PAGE4 amino acid sequence, such as the amino acid sequence set forth as SEQ ID NO: 1.

The immunogenic PAGE4 polypeptides disclosed herein can be chemically synthesized by standard methods, or can be produced recombinantly. An exemplary process for polypeptide production is described in Lu et al., *Federation of European Biochemical Societies Letters*. 429:31-35, 1998. They can also be isolated by methods including preparative chromatography and immunological separations.

An immunogenic PAGE4 polypeptide can be covalently linked to a carrier, which is an immunogenic macromolecule to which an antigenic molecule can be bound. When bound to a carrier, the bound polypeptide becomes more immunogenic. Carriers are chosen to increase the immunogenicity of the bound molecule and/or to elicit higher titers of antibodies against the carrier which are diagnostically, analytically, and/ or therapeutically beneficial. Covalent linking of a molecule to a carrier can confer enhanced immunogenicity and T cell dependence (see Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. Bacterial products and viral proteins (such as hepatitis B surface antigen and core antigen) can also be used as carriers, as well as proteins from higher organisms such as keyhole limpet hemocyanin, horseshoe crab hemocyanin, edestin, mammalian serum albumins, and mammalian immunoglobulins. Additional bacterial products for use as carriers include bacterial wall proteins and other products (for example, streptococcal or staphylococcal cell walls and lipopolysaccharide (LPS)).

Polynucleotides encoding the immunogenic PAGE4 polypeptides disclosed herein are also provided. These polynucleotides include DNA, cDNA and RNA sequences which encode the polypeptide of interest. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, Biochemistry, 3.sup.rd Edition, W.H. 5 Freeman and Co., NY).

A nucleic acid encoding an immunogenic PAGE4 polypeptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, NY, 1989). Polynucleotides also can be isolated by screening genomic or cDNA libraries with probes selected from the sequences of the desired polynucleotide under stringent hybridization conditions.

The polynucleotides encoding an immunogenic PAGE4 polypeptide include a recombinant DNA which is incorporated into a vector into an autonomously replicating plasmid or virus or into the genomic DNA of a prokaryote or eukaryote, or which exists as a separate molecule (such as a cDNA) independent of other sequences. The nucleotides of the invention can be ribonucleotides, deoxyribonucleotides, or modified forms of either nucleotide. The term includes single and double forms of DNA.

In one embodiment, vectors are used for expression of PAGE4 peptides in yeast such as *S. cerevisiae* or *Kluyveromyces lactis*. Several promoters are known to be of use in yeast expression systems such as the constitutive promoters plasma membrane $H^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, many inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2μ) or single copy (CEN) plasmids to give an additional level of control in expression level. The plasmids can include nutritional markers (such as URA3, ADE3, HIS1, and others) for selection in yeast and antibiotic resistance (AMP) for propagation in bacteria. Plasmids for expression on *K. lactis* are known, such as pKLAC1. Thus, in one example, after amplification in bacteria, plasmids can be introduced into the corresponding yeast auxotrophs by methods similar to bacterial transformation.

The PAGE4 peptides can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in yeast lacking the master vacuolar endopeptidase Pep4, which controls the activation of other vacuolar hydrolases. Heterologous expression in strains carrying temperature-sensitive (ts) alleles of genes can be employed if the corresponding null mutant is inviable.

A number of viral vectors have been constructed, including polyoma, i.e., SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,2217,879), alphaviruses (S. Schlesinger, 1993, Trends Biotechnol. 11:18-22; I. Frolov et al., 1996, Proc. Natl. Acad. Sci. USA 93:11371-11377) and retroviruses of avian (Brandyopadhyay et al., 1984, Mol. Cell. Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell. Biol., 5:431-437; Sorge et al., 1984, Mol. Cell. Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

In one embodiment, the polynucleotide encoding an immunogenic PAGE4 polypeptide is included in a viral vector. Suitable vector include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like.

Pox viruses useful in practicing the present invention include orthopox, suipox, avipox, and capripox virus. Orthopox include vaccinia, ectromelia, and raccoon pox. One example of an orthopox of use is vaccinia. Avipox includes fowlpox, canary pox and pigeon pox. Capripox include goatpox and sheeppox. In one example, the suipox is swinepox. Examples of pox viral vectors for expression as described for example, in U.S. Pat. No. 6,165,460, which is incorporated herein by reference. Other viral vectors that can be used include other DNA viruses such as herpes virus and adenoviruses, and RNA viruses such as retroviruses and polio.

In some cases, vaccinia viral vectors may elicit a strong antibody response. Thus, while numerous boosts with vaccinia vectors are possible, its repeated use may not used in certain instances. However, this sensitivity problem can be minimized by using pox from different genera for boosts. In one example, when the first or initial pox virus vector is vaccinia, the second and subsequent pox virus vectors are selected from the pox viruses from a different genus such as suipox, avipox, capripox or an orthopox immunogenically distinct from vaccinia.

The vaccinia virus genome is known in the art. It is composed of a HIND F13L region, TK region, and an HA region. Recombinant vaccinia virus has been used to incorporate an exogenous gene for expression of the exogenous gene product (see, for example, Perkus et al. *Science* 229:981-984, 1985; Kaufman et al. *Int. J. Cancer* 48:900-907, 1991; Moss *Science* 252:1662, 1991). A gene encoding an antigen of interest, such as an immunogenic PAGE4 polypeptide, can be incorporated into the HIND F13L region or alternatively incorporated into the TK region of recombinant vaccinia virus vector (or other nonessential regions of the vaccinia virus genome). Baxby and Paoletti (*Vaccine* 10:8-9, 1992) disclose the construction and use as a vector, of the non-replicating poxvirus, including canarypox virus, fowlpox virus and other avian species. Sutter and Moss (*Proc. Nat'l. Acad. Sci. U.S.A.* 89:10847-10851, 1992) and Sutter et al. (*Virology* 1994) disclose the construction and use as a vector, the non-replicating recombinant Ankara virus (MVA, modified vaccinia Ankara).

Suitable vectors are disclosed, for example, in U.S. Pat. No. 6,998,252, which is incorporated herein by reference. In one example, a recombinant poxvirus, such as a recombinant vaccinia virus is synthetically modified by insertion of a chimeric gene containing vaccinia regulatory sequences or DNA sequences functionally equivalent thereto flanking DNA sequences which to nature are not contiguous with the flanking vaccinia regulatory DNA sequences that encode an immunogenic PAGE4 polypeptide. The recombinant virus containing such a chimeric gene is effective at expressing the immunogenic PAGE4 polypeptide. In one example, the vaccine viral vector comprises (A) a segment comprised of (i) a first DNA sequence encoding an immunogenic PAGE4 polypeptide and (ii) a poxvirus promoter, wherein the poxvirus promoter is adjacent to and exerts transcriptional control over the DNA sequence encoding an immunogenic PAGE4 polypeptide; and, flanking said segment, (B) DNA from a nonessential region of a poxvirus genome. The viral vector can encode a selectable marker. In one example, the poxvirus includes, for example, a thymidine kinase gene (see U.S. Pat. No. 6,998,252, which is incorporated herein by reference).

Poxyiral vectors that encode an immunogenic PAGE4 polypeptide include at least one expression control element operationally linked to the nucleic acid sequence encoding the PAGE4 polypeptide. The expression control elements are inserted in the poxyiral vector to control and regulate the expression of the nucleic acid sequence. Examples of expression control elements of use in these vectors includes, but is not limited to, lac system, operator and promoter regions of phage lambda, yeast promoters and promoters derived from polyoma, adenovirus, retrovirus or SV40. Additional operational elements include, but are not limited to, leader sequence, termination codons, polyadenylation signals and any other sequences necessary or preferred for the appropriate transcription and subsequent translation of the nucleic acid sequence encoding the immunogenic PAGE4 polypeptide in the host system. The expression vector can contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in "Current Protocols in Molecular Biology", John Wiley and Sons, New York, N.Y.) and are commercially available.

Basic techniques for preparing recombinant DNA viruses containing a heterologous DNA sequence encoding the immunogenic PAGE4 polypeptide, are known in the art. Such techniques involve, for example, homologous recombination between the viral DNA sequences flanking the DNA sequence in a donor plasmid and homologous sequences present in the parental virus (Mackett et al., 1982, Proc. Natl. Acad. Sci. USA 79:7415-7419). In particular, recombinant viral vectors such as a poxyiral vector can be used in delivering the gene. The vector can be constructed for example by steps known in the art, such as steps analogous to the methods for creating synthetic recombinants of the fowlpox virus described in U.S. Pat. No. 5,093,258, incorporated herein by reference. Other techniques include using a unique restriction endonuclease site that is naturally present or artificially inserted in the parental viral vector to insert the heterologous DNA.

Generally, a DNA donor vector contains the following elements: (i) a prokaryotic origin of replication, so that the vector may be amplified in a prokaryotic host; (ii) a gene encoding a marker which allows selection of prokaryotic host cells that contain the vector (e.g., a gene encoding antibiotic resistance); (iii) at least one DNA sequence encoding the PAGE4 polypeptide located adjacent to a transcriptional promoter capable of directing the expression of the sequence; and (iv) DNA sequences homologous to the region of the parent virus genome where the foreign gene(s) will be inserted, flanking the construct of element (iii). Methods for constructing donor plasmids for the introduction of multiple foreign genes into pox virus are described in WO91/19803, incorporated herein by reference.

Generally, DNA fragments for construction of the donor vector, including fragments containing transcriptional promoters and fragments containing sequences homologous to the region of the parent virus genome into which foreign DNA sequences are to be inserted, can be obtained from genomic DNA or cloned DNA fragments. The donor plasmids can be mono, di-, or multivalent (i.e., can contain one or more inserted foreign DNA sequences). The donor vector can contain an additional gene that encodes a marker that will allow identification of recombinant viruses containing inserted foreign DNA. Several types of marker genes can be used to permit the identification and isolation of recombinant viruses. These include genes that encode antibiotic or chemical resistance (e.g., see Spyropoulos et al., 1988, J. Virol. 62:1046; Falkner and Moss, 1988, J. Virol. 62:1849; Franke et al., 1985, Mol. Cell. Biol. 5:1918), as well as genes such as the *E. coli* lacZ gene, that permit identification of recombinant viral plaques by colorimetric assay (Panicali et al., 1986, Gene 47:193-199).

The DNA gene sequence to be inserted into the virus can be placed into a donor plasmid, such as an *E. coli* or a *Salmonella* plasmid construct, into which DNA homologous to a section of DNA such as that of the insertion site of the poxvirus where the DNA is to be inserted has been inserted. Separately the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA that is the desired insertion region. With a parental pox viral vector, a pox promoter is used. The resulting plasmid construct is then amplified by growth within *E. coli* bacteria and isolated. Next, the isolated plasmid containing the DNA gene sequence to be inserted is transfected into a cell culture, for example chick embryo fibroblasts, along with the parental virus, for example poxvirus. Recombination between homologous pox DNA in the plasmid and the viral genome respectively results in a recombinant poxvirus modified by the presence of the promoter-gene construct in its genome, at a site that does not affect virus viability.

As noted above, the DNA sequence is inserted into a region (insertion region), in the virus that does not affect virus viability of the resultant recombinant virus. One of skill in the art can readily identify such regions in a virus by, for example, randomly testing segments of virus DNA for regions that allow recombinant formation without seriously affecting virus viability of the recombinant. One region that can readily be used and is present in many viruses is the thymidine kinase (TK) gene. The TK gene has been found in all pox virus genomes examined, including leporipoxvirus (Upton et al., 1986, J. Virology 60:920); shope fibromavirus; capripoxvirus (Gershon et al., 1989, J. Gen. Virol. 70:525) Kenya sheep-1; orthopoxvirus (Weir et al., 1983, J. Virol. 46:530) vaccinia (Esposito et al., 1984, Virology 135:561); monkeypox and variola virus (Hruby et al., 1983, PNAS 80:3411) vaccinia (Kilpatrick et al., 1985, Virology 143:399); Yaba monkey tumor virus; avipoxvirus (Binns et al., 1988, J. Gen. Virol. 69:1275); fowipox; (Boyle et al., 1987, Virology 156:355); fowlpox (Schnitzlein et al., 1988, J. Virological Methods 20:341); fowlpox, quailpox; entomopox (Lytvyn et al., 1992, J. Gen. Virol. 73:3235-3240).

In vaccinia, in addition to the TK region, other insertion regions include, for example, the HindIII M fragment. In fowlpox, in addition to the TK region, other insertion regions include, for example, the BamHI J fragment (Jenkins et al., 1991, AIDS Research and Human Retroviruses 7:991-998) the ECORO-HindIII fragment, EcoRV-HindIII fragment, BamHI fragment and the HindIII fragment set forth in EPO Application No. 0 308220 A1 (see also Calvert et al., 1993, J. Virol. 67:3069-3076; Taylor et al., 1988, Vaccine 6:497-503; Spehner et al., 1990; Boursnell et al., 1990, J. Gen. Virol. 71:621-628).

In swinepox, insertion sites include the thymidine kinase gene region. In addition to the requirement that the gene be inserted into an insertion region, successful expression of the inserted gene by the modified poxvirus requires the presence of a promoter operably linked to the desired gene. Generally, the promoter must be placed so that it is located upstream from the gene to be expressed. Promoters are well known in the art and can readily be selected depending on the host and the cell type you wish to target. In one example, in poxviruses, pox viral promoters are used, such as the vaccinia 7.5K, 40K or fowlpox promoters such as FPV CIA. Enhancer elements can also be used in combination to increase the level of expression. Furthermore, inducible promoters can be utilized.

Homologous recombination between donor plasmid DNA and viral DNA in an infected cell results in the formation of recombinant viruses that incorporate the desired elements. Appropriate host cells for in vivo recombination are generally eukaryotic cells that can be infected by the virus and transfected by the plasmid vector. Examples of such cells suitable for use with a pox virus are chick embryo fibroblasts, HuTK143 (human) cells, and CV-1 and BSC-40 (both monkey kidney) cells. Infection of cells with pox virus and transfection of these cells with plasmid vectors is accomplished by techniques standard in the art (see U.S. Pat. No. 4,603,112 and PCT Publication No. WO89/03429).

Following in vivo recombination, recombinant viral progeny can be identified by one of several techniques. For example, if the DNA donor vector is designed to insert foreign genes into the parent virus thymidine kinase (TK) gene, viruses containing integrated DNA will be TK- and can be selected on this basis (Mackett et al., 1982, Proc. Natl. Acad. Sci. USA 79:7415). Alternatively, co-integration of a gene encoding a marker or indicator gene with the foreign gene(s) of interest, as described above, can be used to identify recombinant progeny. One preferred indicator gene is the *E. coli* lacZ gene. Recombinant viruses expressing beta-galactosidase can be selected using a chromogenic substrate for the enzyme (Panicali et al., 1986, Gene 47:193). Once a recombinant virus has been identified, a variety of well-known methods can be used to assay the expression of the immunogenic PAGE4 sequence encoded by the inserted DNA fragment. These methods include black plaque assay (an in situ enzyme immunoassay performed on viral plaques), Western blot analysis, radioimmunoprecipitation (RIPA), and enzyme immunoassay (EIA).

This disclosure encompasses a recombinant virus comprising more than one antigen of interest for the purpose of having a multivalent vaccine. For example, the recombinant virus may comprise the virus genome or portions thereof, the nucleic acid sequence encoding the immunogenic PAGE4 polypeptide and a nucleic acid sequence encoding a hepatitis B surface antigen.

In one embodiment, a composition is provided that includes a recombinant virus comprising a vaccinia virus genome or portions thereof, the nucleic acid sequence encoding an immunogenic PAGE4 polypeptide and a recombinant virus comprising the nucleic acid sequence encoding the immunostimulatory molecule, B 7-1 alone or in combination with the nucleic acid sequence encoding the immunostimulatory molecule, B7-2, or a recombinant virus containing both the genes for a tumor antigen and an immunostimulatory molecule. This disclosure also encompasses a recombinant virus comprising the immunogenic PAGE4 polypeptide that is administered with a second recombinant virus comprising the virus genome or portion thereof, and one or more nucleic acid sequences encoding one or more B7 molecules, such as a recombinant vaccinia virus expressing B7-1 and/or B7-2. It is disclosed in U.S. Pat. No. 893,869 (incorporated by reference herein) that the rapid infection of tumor cells with these recombinant viruses demonstrates that vaccinia can authentically express these proteins and that they are functional molecules. Following transfer of the nucleic acids, weakly immunogenic syngeneic tumors expressing these recombinant molecules are rejected by immunocompetent hosts.

Thus, in one example, recombinant virus is disclosed that is a recombinant vaccinia virus containing B7-1 and a recombinant vaccinia virus containing B7-2 (designated rV-B7-1 and rV-B7-2, respectively); the composition can include rV-B7-1 and/or rV-B7-2 in combination with an immunogenic PAGE4 polypeptide.

The B7 molecule includes but is not limited to B7-1, B7-2 and the like and analogs thereof. The B7 gene may be cloned from mammalian sources, including but not limited to mammalian tissues, genomic libraries or cDNA libraries, preferably from murine or human sources. Co-stimulatory molecules of the B7 family (namely B7-1, B7-2, and possibly B7.3) are believed to be members of the immunoglobulin gene superfamily. These molecules are present on macrophages, dendritic cells, monocytes (antigen presenting cells (APCs)). Significant amplification of the immune response against a given antigen generally does not occur without co-stimulation (June et al. (*Immunology Today* 15:321-331, 1994); Chen et al. (*Immunology Today* 14:483-486); Townsend et al. (*Science* 259:368-370)). Freeman et al. (*J. Immunol.* 143:2714-2722, 1989) report cloning and sequencing of B7-1 gene. Azuma et al. Nature 366:76-79, 1993) report cloning and sequencing B7-2 gene. Thus, in one embodiment the B7-1 gene or the B7-2 genes are administered in conjunction with the immunogenic PAGE4 polypeptide. The insertion of nucleic acids encoding B7-1 and B7-2 into vaccinia virus has been disclosed (see for example, U.S. Pat. No. 6,893,869, incorporated herein by reference; this U.S. Patent also discloses the use of a nucleic acid encoding IL-2 in a vaccinia virus). Several vectors including IL-2, B7-1 and B7-2 have been deposited with the American Type Culture Collection (ATCC), 12301 Parklawn Drive, Rockville, Md. on Oct. 3, 1994 under the terms of the Budapest Treaty (for example, rV-CEA/$_n$IL-2 (ATCC Designation VR 2480), rV-$_m$B7-2 (ATCC Designation VR 2482); and rV-$_m$B7-1 (ATCC Designation VR 2483)).

DNA sequences encoding an immunogenic PAGE4 polypeptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

As noted above, a polynucleotide sequences encoding an immunogenic PAGE4 polypeptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

Hosts can include microbial, yeast, insect and mammalian organisms. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, Jakoby and Pastan (eds), 1979, Cell Culture. Methods in Enzymology, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although cell lines may be used, such as cells designed to provide higher expression desirable glycosylation patterns, or other features.

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the CaCl$_2$ method using procedures well known in the art. Alternatively, MgCl$_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding an immunogenic PAGE4 polypeptide, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Therapeutic Methods and Pharmaceutical Compositions

An immunogenic PAGE4 polypeptide as disclosed herein, or a nucleic acid encoding the immunogenic PAGE4 polypeptide, can be administered to a subject in order to generate an immune response.

In exemplary applications, compositions are administered to a patient suffering from a disease, such as a reproductive cancer (for example, prostate, cervical, testicular or uterine cancer), in an amount sufficient to raise an immune response to PAGE4-expressing cells. Administration induces a sufficient immune response to slow the proliferation of such cells or to inhibit their growth, or to reduce a sign or a symptom of the tumor. Amounts effective for this use will depend upon the severity of the disease, the general state of the patient's health, and the robustness of the patient's immune system. A therapeutically effective amount of the compound is that which provides either subjective relief of a symptom(s) or an objectively identifiable improvement as noted by the clinician or other qualified observer.

An immunogenic PAGE4 polypeptide can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995) either locally or systemically, such as by intramuscular, subcutaneous, or intravenous injection, but even oral, nasal, or anal administration is contemplated. In one embodiment, administration is by subcutaneous or intramuscular injection. To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. (see, e.g., Banga, supra). A particulate carrier based on a synthetic polymer has been shown to act as an adjuvant to enhance the immune response, in addition to providing a controlled release. Aluminum salts can also be used as adjuvants to produce an immune response.

In one specific, non-limiting example, an immunogenic PAGE4 polypeptide is administered in a manner to direct the immune response to a cellular response (that is, a cytotoxic T lymphocyte (CTL) response), rather than a humoral (antibody) response.

Optionally, one or more cytokines, such as interleukin (IL)-2, IL-6, IL-12, IL-15, RANTES, granulocyte macrophage colony stimulating factor (GM-CSF), tumor necrosis factor (TNF)-α, interferon (IFN)-α or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 41 BBL, or combinations of these molecules, can be used as biological adjuvants (see, for example, Salgaller et al., 1998, J. Surg. Oncol. 68(2):122-38; Lotze et al., 2000, Cancer J. Sci. Am. 6 (Suppl 1):S61-6; Cao et al., 1998, Stem Cells 16 (Suppl 1):251-60; Kuiper et al., 2000, Adv. Exp. Med. Biol. 465:381-90). These molecules can be administered systemically (or locally) to the host. In several examples, IL-2, RANTES, GM-CSF, TNF-α, IFN-γ, G-CSF, LFA-3, CD72, B7-1, B7-2, B7-1 B.7-2, OX-40L, 41 BBL and ICAM-1 are administered.

A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (for example, via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, E. coli lipoproteins, such as tripalmitoyl-S-glycerylcysteinyl-seryl-serine can be used to prime tumor specific CTL when covalently attached to an appropriate peptide (see, Deres et al., Nature 342:561, 1989). Further, as the induction of neutralizing antibodies can also be primed with the same molecule conjugated to a peptide which displays an appropriate epitope, two compositions can be combined to elicit both humoral and cell-mediated responses where that is deemed desirable.

In yet another embodiment, to induce a CTL response to an immunogenic PAGE4 polypeptide, a MHC Class II-restricted T-helper epitope is added to the immunogenic PAGE4 polypeptide to induce T-helper cells to secrete cytokines in the microenvironment to activate CTL precursor cells. The technique further involves adding short lipid molecules to retain the construct at the site of the injection for several days to localize the antigen at the site of the injection and enhance its proximity to dendritic cells or other "professional" antigen presenting cells over a period of time (see Chesnut et al., "Design and Testing of Peptide-Based Cytotoxic T-Cell-Mediated Immunotherapeutics to Treat Infectious Diseases and Cancer," in Powell et al., eds., Vaccine Design, the Subunit and Adjuvant Approach, Plenum Press, New York, 1995).

A pharmaceutical composition including an immunogenic PAGE4 polypeptide is thus provided. In one embodiment, the immunogenic PAGE4 polypeptide is mixed with an adjuvant containing two or more of a stabilizing detergent, a micelle-forming agent, and an oil. Suitable stabilizing detergents, micelle-forming agents, and oils are detailed in U.S. Pat. Nos. 5,585,103; 5,709,860; 5,270,202; and 5,695,770, all of which are incorporated by reference. A stabilizing detergent is any detergent that allows the components of the emulsion to remain as a stable emulsion. Such detergents include polysorbate, 80 (TWEEN) (Sorbitan-mono-9-octadecenoate-poly(oxy-1,2-ethanediyl; manufactured by ICI Americas, Wilmington, Del.), TWEEN 40™, TWEEN 20™, TWEEN 60™, ZWITTERGENT™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, e.g., Schmolka, J. Am. Oil. Chem. Soc. 54:110, 1977, and Hunter et al., J. Immunol. 129:1244, 1981, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, J. Immun. 133:3167, 1984. The agent can be provided in an effective amount, for example between 0.5 and 10%, or in an amount between 1.25 and 5%.

The oil included in the composition is chosen to promote the retention of the antigen in oil-in-water emulsion, i.e., to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse affects, such as granulomas, are evident upon use of the oil.

In one embodiment, the adjuvant is a mixture of stabilizing detergents, micelle-forming agent, and oil available under the name PROVAX® (IDEC Pharmaceuticals, San Diego, Calif.). An adjuvant can also be an immunostimulatory nucleic acid, such as a nucleic acid including a CpG motif, or a biological adjuvant (see above).

Controlled release parenteral formulations can be made as implants, oily injections, or as particulate systems. For a broad overview of protein delivery systems, see Banga, Therapeutic Peptides and Proteins: Formulation, Processing, and Delivery Systems, Technomic Publishing Company, Inc., Lancaster, Pa., 1995. Particulate systems include microspheres, microparticles, microcapsules, nanocapsules, nanospheres, and nanoparticles. Microcapsules contain the therapeutic protein as a central core. In microspheres, the therapeutic agent is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100

µm in diameter and are administered subcutaneously or intramuscularly (see Kreuter, *Colloidal Drug Delivery Systems*, J. Kreuter, ed., Marcel Dekker, Inc., New York, N.Y., pp. 219-342, 1994; Tice & Tabibi, *Treatise on Controlled Drug Delivery*, A. Kydonieus, ed., Marcel Dekker, Inc. New York, N.Y., pp. 315-339, 1992).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. Nos. 5,055,303; 5,188,837; 4,235,871; 4,501,728; 4,837,028; 4,957,735; and 5,019,369; 5,055,303; 5,514,670; 5,413,797; 5,268,164; 5,004,697; 4,902,505; 5,506,206; 5,271,961; 5,254,342; and 5,534,496).

In another embodiment, a pharmaceutical composition includes a nucleic acid encoding an immunogenic PAGE4 polypeptide. A therapeutically effective amount of the immunogenic PAGE4 polynucleotide can be administered to a subject in order to generate an immune response. In one specific, non-limiting example, a therapeutically effective amount of the immunogenic PAGE4 polynucleotide is administered to a subject to treat prostate cancer or breast cancer.

Optionally, one or more cytokines, such as IL-2, IL-6, IL-12, RANTES, GM-CSF, TNF-α, or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 41 BBL, or combinations of these molecules, can be used as biological adjuvants (see, for example, Salgaller et al., 1998, J. Surg. Oncol. 68(2):122-38; Lotze et al., 2000, Cancer J. Sci. Am. 6 (Suppl 1):561-6; Cao et al., 1998, Stem Cells 16 (Suppl 1):251-60; Kuiper et al., 2000, Adv. Exp. Med. Biol. 465:381-90). These molecules can be administered systemically to the host. It should be noted that these molecules can be co-administered via insertion of a nucleic acid encoding the molecules into a vector, for example, a recombinant pox vector (see, for example, U.S. Pat. No. 6,045,802). In various embodiments, the nucleic acid encoding the biological adjuvant can be cloned into same vector as the immunogenic PAGE4 polypeptide coding sequence, or the nucleic acid can be cloned into one or more separate vectors for co-administration. In addition, nonspecific immunomodulating factors such as *Bacillus* Cahnette-Guerin (BCG) and levamisole can be co-administered.

One approach to administration of nucleic acids is direct immunization with plasmid DNA, such as with a mammalian expression plasmid. As described above, the nucleotide sequence encoding an immunogenic PAGE4 polypeptide can be placed under the control of a promoter to increase expression of the molecule.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 µg encapsulated in ISCOMS™ have been found to produce Class I mediated CTL responses (Takahashi et al., *Nature* 344:873, 1990).

In another approach to using nucleic acids for immunization, an immunogenic PAGE4 polypeptide can also be expressed by attenuated viral hosts or vectors or bacterial vectors. Recombinant vaccinia virus, adeno-associated virus (AAV), herpes virus, retrovirus, or other viral vectors can be used to express the peptide or protein, thereby eliciting a CTL response. For example, vaccinia vectors and methods useful in immunization protocols are described in U.S. Pat. No. 4,722,848. BCG (Bacillus Calmette Guerin) provides another vector for expression of the peptides (see Stover, *Nature* 351:456-460, 1991).

A first recombinant virus, such as a poxvirus (for example, vaccine virus) encoding a PAGE4 immunogenic polypeptide can be used in conjunction with a second recombinant virus which has incorporated into a viral genome or infectable portion thereof one or more genes or DNA sequences encoding B7-1, B7-2, or B7-1 and B7-2, wherein the composition is able to coinfect a host cell resulting in coexpression of the polypeptide and the B7-1, B7-2, or B7-1 and B7-2 encoding genes or DNA sequences (see U.S. Pat. Nos. 6,893,869, and 6,045,908, which are incorporated by reference herein). The expression of the B7 gene family has been shown to be an important mechanism of antitumor responses in both mice and humans.

When a viral vector is utilized, it is desirable to provide the recipient with a dosage of each recombinant virus in the composition in the range of from about $10^5$ to about $10^{10}$ plaque forming units/mg mammal, although a lower or higher dose can be administered. The composition of recombinant viral vectors can be introduced into a mammal either prior to any evidence of a tumor, such as prostate, uterine or testicular cancer, or to mediate regression of the disease in a mammal afflicted with the tumor. Examples of methods for administering the composition into mammals include, but are not limited to, exposure of cells to the recombinant virus ex vivo, or injection of the composition into the affected tissue or intravenous, subcutaneous, intradermal or intramuscular administration of the virus. Alternatively the recombinant viral vector or combination of recombinant viral vectors may be administered locally by direct injection into the cancerous lesion in a pharmaceutically acceptable carrier. Generally, the quantity of recombinant viral vector, carrying the nucleic acid sequence of one or more immunogenic PAGE4 polypeptides to be administered is based on the titer of virus particles. An exemplary range of the immunogen to be administered is $10^5$ to $10^{10}$ virus particles per mammal, such as a human.

In the embodiment where a combination of a first recombinant viral vector carrying a nucleic acid sequence of one or more immunogenic PAGE4 polypeptide and a second recombinant viral vector carrying the nucleic acid sequence of one or more immunostimulatory molecules is used, the mammal can be immunized with different ratios of the first and second recombinant viral vector. In one embodiment the ratio of the first vector to the second vector is about 1:1, or about 1:3, or about 1:5. Optimal ratios of the first vector to the second vector may easily be titered using the methods known in the art (see, for example, U.S. Pat. No. 6,893,869, incorporated herein by reference).

In one embodiment the recombinant viruses have been constructed to express cytokines (such as TNF-α, IL-6, GM-CSF, and IL-2), and co-stimulatory and accessory molecules (B7-1, B7-2) alone and in a variety of combinations. Simultaneous production of an immunostimulatory molecule and the immunogenic PAGE4 polypeptide enhances the generation of specific effectors. Without being bound by theory, dependent upon the specific immunostimulatory molecules, different mechanisms might be responsible for the enhanced immunogenicity: augmentation of help signal (IL-2), recruitment of professional APC (GM-CSF), increase in CTL frequency (IL-2), effect on antigen processing pathway and MHC expression (IFNγ and TNFα) and the like. For example, IL-2, IL-6, interferon, tumor necrosis factor, or a nucleic acid encoding these molecules, can be administered in conjunction with a PAGE4 immunogenic polypeptide, or a nucleic acid encoding a PAGE4 polypeptide. The co-expression of an immunogenic PAGE4 polypeptide together with at least one immunostimulatory molecule can be effective in an animal model to show anti-tumor effects.

In one embodiment, a nucleic acid encoding an immunogenic PAGE4 polypeptide is introduced directly into cells. For example, the nucleic acid can be loaded onto gold microspheres by standard methods and introduced into the skin by a device such as Bio-Rad's Helios™ Gene Gun. The nucleic acids can be "naked," consisting of plasmids under control of a strong promoter. Typically, the DNA is injected into muscle, although it can also be injected directly into other sites, including tissues in proximity to metastases. Dosages for injection are usually around 0.5 µg/kg to about 50 mg/kg, and typically are about 0.005 mg/kg to about 5 mg/kg (see, e.g., U.S. Pat. No. 5,589,466).

In one specific, non-limiting example, a pharmaceutical composition for intravenous administration would include about 0.1 µg to 10 mg of immunogenic PAGE4 polypeptide per patient per day. Dosages from 0.1 up to about 100 mg per patient per day can be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remingtons Pharmaceutical Sciences*, 19th Ed., Mack Publishing Company, Easton, Pa., 1995.

Single or multiple administrations of the compositions are administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of disease without producing unacceptable toxicity to the subject. Systemic or local administration can be utilized.

In another method, antigen presenting cells (APCs), such as dendritic cells, are pulsed or co-incubated with peptides comprising an immunogenic PAGE4 polypeptide in vitro. In one specific, non-limiting example, the antigen presenting cells can be autologous cells. A therapeutically effective amount of the antigen presenting cells can then be administered to a subject.

The immunogenic PAGE4 polypeptide can be delivered to the dendritic cells or to dendritic cell precursors via any method known in the art, including, but not limited to, pulsing dendritic cells directly with antigen, or utilizing a broad variety of antigen delivery vehicles, such as, for example, liposomes, or other vectors known to deliver antigen to cells. In one specific, non-limiting example an antigenic formulation includes about 0.1 µg to about 1,000 µg, or about 1 to about 100 µg of a selected immunogenic PAGE4 polypeptide. The immunogenic PAGE4 polypeptide can also be administered with agents that promote dendritic cell maturation. Specific, non-limiting examples of agents of use are interleukin-4 (IL-4) and granulocyte/macrophage colony stimulating factor (GM-CSF), or flt-3 ligand (flt-3L). The preparation can also contain buffers, excipients, and preservatives, amongst other ingredients.

In one embodiment, mature antigen presenting cells are generated to present the immunogenic PAGE4 polypeptide. These dendritic cells are then administered alone to a subject with a tumor that expresses PAGE4, such as a prostate or a breast cancer. In another embodiment, the mature dendritic cells are administered in conjunction with a chemotherapeutic agent.

Alternatively, the APCs are used to sensitize CD8 cells, such as tumor infiltrating lymphocytes (TILs) from prostate or breast tumors or peripheral blood lymphocytes (PBLs). The TILs or PBLs can be from the same subject (autologous) that is to be treated. Alternatively, the TILs or PBLs can be heterologous. However, they should at least be MHC Class-I restricted to the HLA types the subject possesses. An effective amount of the sensitized cells are then administered to the subject.

Peripheral blood mononuclear cells (PBMCs) can be used as the responder cell source of CTL precursors. The appropriate antigen-presenting cells are incubated with peptide, after which the peptide-loaded antigen-presenting cells are then incubated with the responder cell population under optimized culture conditions. Positive CTL activation can be determined by assaying the culture for the presence of CTLs that kill radio-labeled target cells, both specific peptide-pulsed targets as well as target cells expressing endogenously processed forms of the antigen from which the peptide sequence was derived, such as PAGE4 (for example, SEQ ID NO: 1).

The cells can be administered to a subject to inhibit the growth of cells of PAGE4 expressing tumors. In these applications, a therapeutically effective amount of activated antigen presenting cells, or activated lymphocytes, are administered to a subject suffering from a disease, in an amount sufficient to raise an immune response to PAGE4-expressing cells. The resulting immune response is sufficient to slow the proliferation of such cells or to inhibit their growth, or to reduce a sign or a symptom of the tumor.

In a supplemental method, any of these immunotherapies is augmented by administering a cytokine, such as interleukin (IL)-2, IL-3, IL-6, IL-10, IL-12, IL-15, GM-CSF, interferons.

In a further method, any of these immunotherapies is augmented by administering an additional chemotherapeutic agent. In one example, this administration is sequential. Examples of such agents are alkylating agents, antimetabolites, natural products, or hormones and their antagonists. Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine). Examples of antimetabolites include folic acid analogs (such as methotrexate), pyrimidine analogs (such as 5-FU or cytarabine), and purine analogs, such as mercaptopurine or thioguanine. Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocyin C), and enzymes (such as L-asparaginase). Examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide). Examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testosterone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol. Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Reagents for the Detection of Cells that Express CD8 (CD8+) Cells that Specifically Bind PAGE4

Reagents are provided herein for the detection of CD8 expressing cells that specifically bind PAGE4. These reagents are tetrameric MHC Class I/immunogenic PAGE4 polypeptide complexes. These tetrameric complexes include an immunogenic PAGE4 polypeptide that includes at most ten, such as nine, consecutive amino acids from the consensus sequence:

MSARVRSRSRGRGDGX$_1$X$_2$APDVVAFVAPGESQQEEPPTDNQDIE

PGQEREGTPPIEERKX$_3$X$_4$GDCQEMDX$_5$EKTRSERGDGSDVKEX$_6$X$_7$PPN

PKHX$_8$KTKEAGDGQP (SEQ ID NO: 1 ,PAGE4 CONSENSUS

SHOWING SUBSTITUTIONS)

wherein X1 is Q or Y, X2 is E or L, X3 is V or Y, X4 is E or L, X5 is V or L, X6 is K or Y, X7 is T or L, and X8 is A or V and wherein the polypeptide comprises one of (a) amino acids 16 to 25 of SEQ ID NO: 1, (b) amino acids 59 to 68 of SEQ ID NO: 1, or (c) amino acids 84 to 92 of SEQ ID NO: 1. Specific examples of immunogenic PAGE4 polypeptide that are nine amino acids in length are disclosed above.

The tetrameric complexes disclosed herein do not include additional consecutive amino acids of PAGE4 (SEQ ID NO: 1), such that the polypeptide does not include the full length PAGE4 amino acid sequence.

Tetrameric MHC Class I/peptide complexes can be synthesized using methods well known in the art (Altmann et al., *Science* 274:94, 1996, which is herein incorporated by reference). In one specific non-limiting example, purified HLA heavy chain and β2-microglobulin (β2m) can be synthesized by means of a prokaryotic expression system. One specific, non-limiting example of an expression system of use is the pET system (R&D Systems, Minneapolis, Minn.). The heavy chain is modified by deletion of the trans-membrane and cytosolic tail and COOH-terminal addition of a sequence containing the biotin protein ligase (Bir-A) enzymatic biotinylation site. Heavy chain, γ2m, and peptide are then refolded. The refolded product can be isolated by any means known in the art, and then biotinylated by Bir-A. A tetramer is then produced by contacting the biotinylated product with strepavidin.

In one embodiment, the strepavidin is labeled. Suitable labels include, but are not limited to, enzymes, magnetic beads, colloidal magnetic beads, haptens, fluorochromes, metal compounds, radioactive compounds or drugs. The enzymes that can be conjugated to strepavidin include, but are not limited to, alkaline phosphatase, peroxidase, urease and β-galactosidase. The fluorochromes that can be conjugated to the strepavidin include, but are not limited to, fluorescein isothiocyanate, tetramethylrhodamine isothiocyanate, phycoerythrin, allophycocyanins and Texas Red. For additional fluorochromes that can be conjugated to strepavidin, see Haugland, R. P., *Molecular Probes: Handbook of Fluorescent Probes and Research Chemicals* (1992-1994). The metal compounds that can be conjugated to the strepavidin include, but are not limited to, ferritin, colloidal gold, and particularly, colloidal superparamagnetic beads. The haptens that can be conjugated to the strepavidin include, but are not limited to, biotin, digoxigenin, oxazalone, and nitrophenol. The radioactive compounds that can be conjugated to strepavidin are known to the art, and include but are not limited to technetium 99m ($^{99}$Tc), $^{125}$I and amino acids comprising any radionuclides, including, but not limited to, $^{14}$C, $^{3}$H and $^{35}$S. Generally, strepavidin labeled with a fluorochrome is utilized in the methods disclosed herein.

In one embodiment, suspension of cells including T cells that specifically recognize PAGE4 is produced, and the cells are reacted with the tetramer in suspension. In one embodiment, these reagents are used to label cells, which are then analyzed by fluorescence activated cell sorting (FACS). A machine for FACS employs a plurality of color channels, low angle and obtuse light-scattering detection channels, and impedance channels, among other more sophisticated levels of detection, to separate or sort cells. Any FACS technique can be employed as long as it is not detrimental to the detection of the desired cells. (For exemplary methods of FACS see U.S. Pat. No. 5,061,620.)

The disclosure is illustrated by the following non-limiting Examples.

EXAMPLES

To develop more effective immunotherapy for the cancer patients, it is important to find new tumor-specific antigens and establishing new vaccine strategies are important. A new potential prostate cancer target, PAGE4 (prostate associated gene 4), was identified by analysis of expressing sequence tag (ESTs) databases and a functional genomic approach (Brinkmann et al, Proc Natl Acad Sci USA 1998; 95:10757-62; Brinkmann et al., Cancer Res 1999; 59:1445-8). The PAGE4 gene belongs to the GAGE/PAGE family, and five homologous PAGE genes were identified (Brinkmann et al, Proc Natl Acad Sci USA 1998; 95:10757-62; Brinkmann et al., Cancer Res 1999; 59:1445-8). The PAGE4 transcript has a predicted open reading frame of 102 amino acids, and the Mr 16,000 protein product of PAGE4 is localized in the cytoplasm of the cell. PAGE4 is an X chromosome-linked cancer-testis (CT) antigen expressed in normal testis, normal prostate, normal uterus, and highly expressed in prostate and uterine cancer (Brinkmann et al, Proc Natl Acad Sci USA 1998; 95:10757-62, Iavarone et al., Mol Cancer Ther 2002; 1:329-35). The expression was also reported in placenta and fallopian tube, and was found no expression in the other normal tissues (Brinkmann et al, Proc Natl Acad Sci USA 1998; 95:10757-62).

Cancer testis antigens are primarily expressed in the primitive germ cells, spermatogonia, in the normal testis. Malignant transformation is often associated with activation or derepression of silent CT genes, and this results in the expression of CT antigens in a variable proportion of a wide range of human tumors. Because of the blood-testis barrier (Bart et al., Lancet Oncol 2002; 3:357-363, Zendman et al., J Cell Physiol 2003; 194: 272-88.) and since germline cells do not express the classical HLA molecules (Fiszer et al., Am J Reprod Immunol 1998; 40:172-176; Mintz et al., Crit Rev Oncog 2000; 11:77-95), expression of CT antigens in normal testis does not lead to T-cell activation and thus makes CT antigens attractive candidates for cancer vaccines (Moingeon, P. Cancer vaccines. Vaccine 2001; 19:1305-26). CTL epitopes of a number of CT antigens have been identified. Cancer testis antigens such as NY-ESO-1, MAGE and SSX2 have been reported to elicit spontaneous humoral and cellular immune responses in cancer patients (Jäger et al., J. Exp. Med. 1998; 187:265-270; Ayyoub et al., J. Immunol. 2002; 168:1717-1722; Nakada et al., Cancer Immun 2003; 3:10). Clinical trials targeting NY-ESO-1 and MAGE have been conducted using recombinant protein, peptide, recombinant virus encoding antigen, or peptide-pulsed dendritic cells. Immune responses to these antigens have been demonstrated in vaccinated patients (Jäger et al., Proc. Natl. Acad. Sci. U.S.A 2000; 97:12198-12203; Atanackovic et al., J. Immunol. 2004; 172:3289-3296; Davis et al., Proc. Natl. Acad. Sci. U.S.A 2004; 101: 10697-10702; Lonchay et al., Proc. Natl. Acad. Sci. U.S.A 2004; 101:14631-14638).

The study described here reports the identification and characterization of a novel PAGE4 immunogenic polypeptides, and the generation of an enhancer agonist of this epitope. T-cell lines generated from prostate cancer patients using the agonist peptide, showed high levels of lysis of PAGE4-expressing tumor cells and enhanced secretion of IFN-γ, granzyme B, TNF-α, IL-2, and lymphotactin.

The disclosure is illustrated by the following non-limiting Examples.

Example 1

Materials and Methods

Cell Cultures: The human prostate carcinoma cell lines LNCaP (HLA-A2 positive and PAGE4 positive), 22Rv1 (HLA-A2 negative and PAGE4 positive), a human breast carcinoma cell line MCF-7 (HLA-A2 positive and PAGE4 negative) and a human pancreatic adenocarcinoma cell line AsPC-1 (HLA-A2 negative and PAGE4 negative) were purchased from American Type Culture Collection (Manassas, Va.). The cultures were free of mycoplasma and were maintained in complete medium [RPMI 1640 (Mediatech, Inc., Herndon, Va.) supplemented with 10% fetal bovine serum, 2 mM glutamine, 100 units/ml penicillin, and 100 μg/ml streptomycin (Mediatech, Inc.)]. PC3/PAGE4 cells [PC3 cells, a prostate carcinoma cell line transfected with a full-length PAGE4 gene] (Iavarone et al., Mol Cancer Ther 2002; 1:329-35) were maintained in the complete medium with 0.5 μg/ml puromycin (Invitrogen, Carlsbad, Calif.). The T2 cells transfected with HLA-A2 gene (Hogan et al., J Exp Med 1988; 168:725-36) were provided by Dr. Peter Cresswell (Yale University School of Medicine, New Haven, Conn.). These cells were mycoplasma free and maintained in Iscove's modified Dulbecco's complete medium (Mediatech, Inc.).

Peptides: The amino acid sequence of PAGE4 was scanned for matches to consensus motifs for HLA-A2 binding peptides. The computer algorithm that was used was from the BioInformatics and Molecule Analysis Section of NIH (BIMAS), developed by Parker et al. (Parker et al., J Immunol 1994; 152:163-75), which ranks potential MHC binding peptides according to the predictive one-half-time dissociation of peptide/MHC complexes. The HLA-A2 allele was chosen because it is the most commonly expressed class I allele. Nine-mer and 10-mer peptides were synthesized if they conformed to the respective consensus motif. A panel of PAGE4 peptides (Table 1), analogues with amino acid substitutions, and MUC-1 peptide (Tsang et al., Clin Cancer Res 2004; 10:2139-49) were made by Biosynthesis Inc. (Lewisville, Texas) with purity>95%.

Flow Cytometry: Dual-color flow cytometric analysis was performed on T-cell lines by using the following antibody combinations: anti-human CD56-FITC/CD8-PE, CD8-FITC/CD45RA-PE, CD8-FITC/CD27-PE, and CD8-FITC/CD28 PE. Antibodies were all purchased from BD Biosciences (San Jose, Calif.). $5 \times 10^5$ cells were washed and resuspended in Ca2+ and Mg2+ free phosphate-buffered saline (PBS). Cells were incubated with the appropriate antibody for 40 min at 4° C. and washed. Samples were analyzed on a FACScan (BD Biosciences).

Tetramer staining: Phycoerythrin (PE)-labeled PAGE4-P16-1/HLA-A*0201 tetramer and control tetramer PE-labeled HIV gag (SLYNTVATL)/HLA-A*0201 were obtained from Beckman Coulter (Fullerton, Calif.). $5 \times 10^5$ T cells were stained with 10 μl of tetramer and anti-CD8 antibody for 30 minutes at room temperature protected from light, and washed and fixed in PBS with 0.5% formaldehyde. $1 \times 10^5$ cells were acquired on a FACSCALIBUR™ flow cytometer (BD Biosciences) and LSRII (BD Biosciences), and data were analyzed using CELL QUEST™ software (BD Biosciences) and FLOWJO™ software (BD Biosciences), respectively.

Peptide Binding to HLA-A2: Binding of PAGE4 peptides and the PAGE4 analogues to HLA-A2 molecules was evaluated by the upregulation of HLA-A2 expression on T2 cells as demonstrated by flow cytometry (Nijman et al., Eur J Immunol 1993; 23:1215-9).

Culture of Dendritic cells from PBMCs: HLA-A2 prostate cancer patient peripheral blood mononuclear cells (PBMCs) were obtained from heparinized blood. PBMCs were separated using lymphocyte separation medium gradient (MP Biomedicals, Aurora, Ohio) following the manufacturer procedure. Dendritic cells (DCs) were prepared using a modification of the procedure described by Sallusto et al. (Sallusto et al., J Exp Med 1994; 179:1109-18).

Generation of T-cell Lines: PBMC from two prostate cancer patients (patient A and B) on a previously described clinical trial utilizing a PSA based vaccine along with radiation therapy for localized or locally advanced prostate cancer (Gulley et al., Clin Cancer Res 2005; 11:3353-62) were used for the generation of T cell lines. Patient A was a 56 year-old black male who had been diagnosed 1 year prior to starting the trial with a Gleason 4+4, T2cN1 tumor and a PSA of 63. At diagnosis, he commenced treatment with a GnRH agonist. When he started on the clinical trial, he had rising PSA despite hormonal therapy. He completed 8 months of study treatment and subsequently was found to have metastatic disease in the liver. He died from progressive disease about 8 months after completing the trial. Patient B was a 59 year-old white male diagnosed with a Gleason 4+3, T1c tumor and a PSA of 8.4. He commenced study treatment 3 months after diagnosis and is alive without evidence of biochemical failure more than 2.5 years following conclusion of therapy. Modification of the protocol described by Tsang et al. (J Natl Cancer Inst 1995; 87:982-90) was used to generate PAGE4-specific CTLs. Irradiated (3000 rad) autologous DCs were used as antigen-presenting cells (APCs). Autologous non-adherent cells were stimulated in the presence of autologous DCs pulsed with peptides at a concentration of 12.5 µg/ml at an effector-to-APC ratio of 10:1. Cultures were maintained for 3 initial days in medium containing 10% human AB serum, and four additional days in the same medium supplemented with 20 units/ml of recombinant human IL-2. After a 7-day culture period, designated as an in vitro stimulation (IVS) cycle, cells were restimulated as described above for a total of 3 IVS. After the third IVS cycle, irradiated (23,000 rads) autologous Epstein-Barr virus (EBV)-transformed B cells were used as APCs. The autologous EBV-transformed B cells were pulsed with 12.5 µg/ml of peptides at an effector-to-APC ratio of 1:3.

Cytotoxic Assay: Cytotoxicity assays were used as described previously (Tsange et al., J Natl Cancer Inst 1995; 87:982-90). A 6-hour or 16-hour $^{111}$In release assay was used to determine T-cell mediated killing. Target cells were labeled with $^{111}$In oxine (Amersham Health, Silver Spring, Md.) for 20 min at room temperature, and used at $3 \times 10^3$ cells per well, in 96-well rounded-bottom culture plates. $^{111}$In released was measured by gamma counting. Spontaneous release was determined by incubating the target cells with medium alone, and complete lysis by incubating the target cells with 2.5% Triton X-100. Specific lysis (%)=[(observed release−spontaneous release)/(complete release−spontaneous release)]×100.

Detection of Cytokines: Supernatants of T cells stimulated for 48 hours with peptide-pulsed autologous EBV-transformed B cells, in IL-2-free medium at various peptide concentrations, were screened for secretion of IFN-γ using an ELISA kit (BioSource International, Camarillo, Calif.) and lymphotactin using an ELISA assay (36). Granzyme B, TNF-α and IL-2 were determined by using a Cytokines and Chemokines-Multiplex Kit (Meso Scale Discovery, Geitherburg, Md.). The results were expressed in pg/ml.

CD107a mobilization assay: The CD107a mobilization assay was performed as previously described (Rubio et al., Nat Med 2003; 9:1377-82). Briefly, $0.5 \times 10^6$ effector cells/ml were incubated with T2 cells pulsed with 12.5 µg/ml of peptide or without peptide at a ratio of 1:4 (E:T) for 5 hours at 37° C. in 5% CO2. CD107a-FITC antibodies (BD Biosciences) for the detection of lysosomal-associated membrane protein-1 (LAMP-1) were added to the cells before incubation. After 1 hr-incubation, 1 µl of monensin (Golgi-Stop, eBioscience, Inc) was added and incubated for an additional 4 h at 37° C. in 5% $CO_2$. Cells were washed and stained with CD8-PE antibodies (BD Biosciences) for 40 min at 4° C. Samples were then fixed and the expression of CD107a on the cell surface of CD8+ T cells was analyzed by flow cytometry.

Infection of target cells with recombinant vaccinia virus: A recombinant vaccinia vector encoding HLA-A2.1 was used for the infection of 22Rv1 cells. This recombinant virus was constructed by the insertion of the HLA-A2.1 gene into the BamHI J region of the genome of the Wyeth strain of vaccinia virus as described (Jenkins et al., AIDS Res Hum Retroviruses 1991; 7:991-998). The gene is under control of the vaccinia 40k promoter (Gritz et al., J Virol 1990; 64:5948-5957). Target cells at a concentration of $2 \times 10^6$ cells/ml in Opti-MEM medium (Invitrogen) were incubated with vaccinia virus at 10 pfu/cell (MOI=10) for 1 hour at 37° C. The cells were then adjusted to a concentration of $5 \times 10^5$/ml in complete medium and incubated for 24 hours at 37° C.

Transfection of target cells with vector containing a full-length PAGE4 cDNA: MCF-7 cells (PAGE4 negative, HLA-A2 positive) were transfected with 1 µg of pcDNA3.1(+) vector containing a full-length PAGE4 cDNA (Chen et al., J Biol Chem 1998; 273:17618-17625) or pcDNA3.1(+) control vector by incubating $2 \times 10^6$ cells/ml with vectors in Opti-MEM medium (Invitrogen) containing lipofectin Reagent (Invitrogen) for 24 hour at 37° C., following the instruction of the manufacturer (Invitrogen). The infected cells were suspended in complete medium and cultured for 24 additional hours.

RT-PCR: For the analysis of PAGE4 expression on tumor cell lines, RT-PCR was performed as described previously (Brinkman et al., Proc Natl Acad Sci USA 1998; 95:10757-62) using the following primers: forward 5'-TTCTAGTTG-CAG CGATGAG-3' (SEQ ID NO: 4) and reverse 5'-CAT-GCTTAGGATTAGGTGG-3' (SEQ ID NO:5).

Statistical Analysis: Statistical analysis of differences between means was done using a two-tailed paired t test (Stat View statistical software, Abacus Concepts, Berkeley, Calif.).

Example 2

Binding Affinity of PAGE4 Peptides and Analogue Peptides to HLA-A2 Molecules

The primary amino acid sequence of human PAGE4 was analyzed for consensus motifs for novel HLA-A2 binding peptides. Two 10-mer peptides (P16-25 designated as P16 and P59-68 designated as P59) and one 9-mer peptide (P84-92 designated as P84) were identified and evaluated (Table 1). Analysis of the primary and secondary HLA-A2 binding anchor amino acid residues at positions 1, 2, 8 and 10 of the native peptides revealed that modification of amino acids at these positions could potentially enhance the binding ability of the peptide to the HLA-A2 molecule. For this reason, five different analogues of native peptides were synthesized and were investigated for their binding ability to HLA-A2-positive T2 cells along with the native P16, P59 and P84 peptides. A MUC-1 peptide and a CEA HLA-A3 binding peptide (CAP-7) were used as a positive and negative control, respectively (Tsang et al., J Natl Cancer Inst 1995; 87:982-90). As shown in Table 1, two of three native peptides (P16, P84) bound to HLA-A2 molecules in the T2 assay.

TABLE 1

Binding of PAGE4 peptides and analogue peptides to HLA-A2 molecules

| Peptides | Designation | Amino acid position See SEQ ID NO: 1 | Peptide sequence | T2 binding[a] |
|---|---|---|---|---|
| P16 (native) | P16 | 16-25 | QEAPDVVAFV | 309 (1.2) |
| P16 (17L) | P16-1 | 16-25 | Q*L*APDVVAFV | 827 (3.2) |
| P16 (16Y/17L) | P16-2 | 16-25 | *YL*APDVVAFV | 790 (3.0) |
| P59 (native) | P59 | 59-68 | VEGDCQEMDL | 246 (0.9) |
| P59 (60L) | P59-1 | 59-68 | V*L*GDCQEMDL | 293 (1.1) |
| P59 (59Y/60L/68V) | P59-2 | 59-68 | *YL*GDCQEMD*V* | 384 (1.5) |
| P84 (native) | P84 | 84-92 | KTPPNPKHA | 270 (1.04) |
| P84 (84Y/85L/92V) | P84-1 | 84-92 | *YL*PPNPKH*V* | 546 (2.1) |
| MUC-1 peptide | (positive control) | | ALWGQDVTSV | 710 (2.7) |
| CAP-7 peptide | (negative control) | | HLFGYSWYK | 260 |

Peptides were used at a concentration of 25 μg/ml. Amino acids are shown by the single-letter code. Substitution amino acids are indicated in bold italic and underlined. MUC-1 peptide is an HLA-A2 binding peptide and CAP-7 is an HLA-A3 binding CEA peptide.
[a]Results are expressed in mean fluorescence intensity (MFI). Values in parentheses are fold increases as compared with the negative control.

The analogues of P16 were designated P16-1 and P16-2, and the analogue of P84 was designated as P84-1. These peptides bound to HLA-A2 at higher levels than their native peptides. Studies were then conducted to examine the ability of these peptides to bind HLA-A2 at various concentrations. As shown in FIG. 1A, P16-1, P16-2 and P84-1 bound to HLA-A2 at higher levels than did the native peptides, at all concentrations. These results indicated that the three analogues with modification in the primary and secondary anchor position were potential agonists of the peptides P16 and P84.

Studies were then undertaken to examine the stability of the peptide-MHC complex for the peptides P16, P84, P16-1, P16-2 and P84-1. Each peptide was incubated with T2 cells overnight, the unbound peptides were washed off, and the cells were then incubated with Brefeldin A to block delivery of new class I molecules to the cell surface. Cells were analyzed for the presence of peptide-HLA-A2 complexes at various time points. As shown in FIG. 1B, for all peptides, more than 43.6% of complexes were remain over the 8-hour observation period. Complexes of P16-2 and P84-1 were more stable than their native peptide complexes over the same period of time. These data indicated that both the binding to the MHC molecule and the stability of the peptide-MHC complex were greater for the P16-1, P16-2 and P84-1 agonist peptides than the native P16 or P84 peptide.

Example 3

Immunogenicity of the PAGE4 Native and Agonist Peptides

Studies were conducted to determine whether T-cell lines could be generated from PBMC from prostate cancer patients . . . . Autologous DCs were used as APC. Five PAGE4-specific T-cell lines were generated from a prostate cancer patient (A) using P16, P16-1, P16-2, P84 and P84-1 peptides (see Example 1). The T-cell lines were designated T-A-P16, T-A-P16-1, T-A-P16-2, T-A-P84 and T-A-P84-1. The specificity of the PAGE4-specific T cells was analyzed for their ability to release IFN-γ after stimulation with autologous B cells pulsed with the corresponding peptides. As shown in Table 2, high levels of IFN-γ production were observed when the T-cell lines were stimulated with the specific peptide.

TABLE 2

Production of IFN-γ by T-cell lines generated from a prostate cancer patient stimulated with P16, P84 and their agonist peptides

| | Production of IFN-γ (pg/ml) | |
|---|---|---|
| T-cell line | Corresponding peptide | None |
| T-A-P16 | 302.0 | <15.6 |
| T-A-P16-1 | 611.6 | <15.6 |
| T-A-P16-2 | 497.0 | <15.6 |
| T-A-P84 | 97.5 | <15.6 |
| T-A-P84-1 | 248.5 | <15.6 |

Cells from five PAGE4-specific T-cell lines established from a prostate cancer patient (patient A) were used as effector cells at in vitro stimulation (IVS-4). These T-cell lines were established by stimulation with P16-pulsed autologous B cells (T-A-P16), P16-1-pulsed autologous B cells (T-A-P16-1), P16-2-pulsed autologous B cells (T-A-P16-2), P84-pulsed autologous B cells (T-A-P84), and P84-1-pulsed autologous B cells (T-A-P84-1). For IFN-γ production, T-cell lines were stimulated with the corresponding peptide at a concentration of 12.5 μg/ml and an effector-to-APC ratio of 1:3. Twenty-four-hour culture supernatants were collected and screened for the secretion of IFN-γ.

The highest levels of IFN-γ production was observed for the T-A-P16-1 T-cell line and the lowest levels of IFN-γ production was observed for the T-A-P84 T-cell line.

Figure 2:
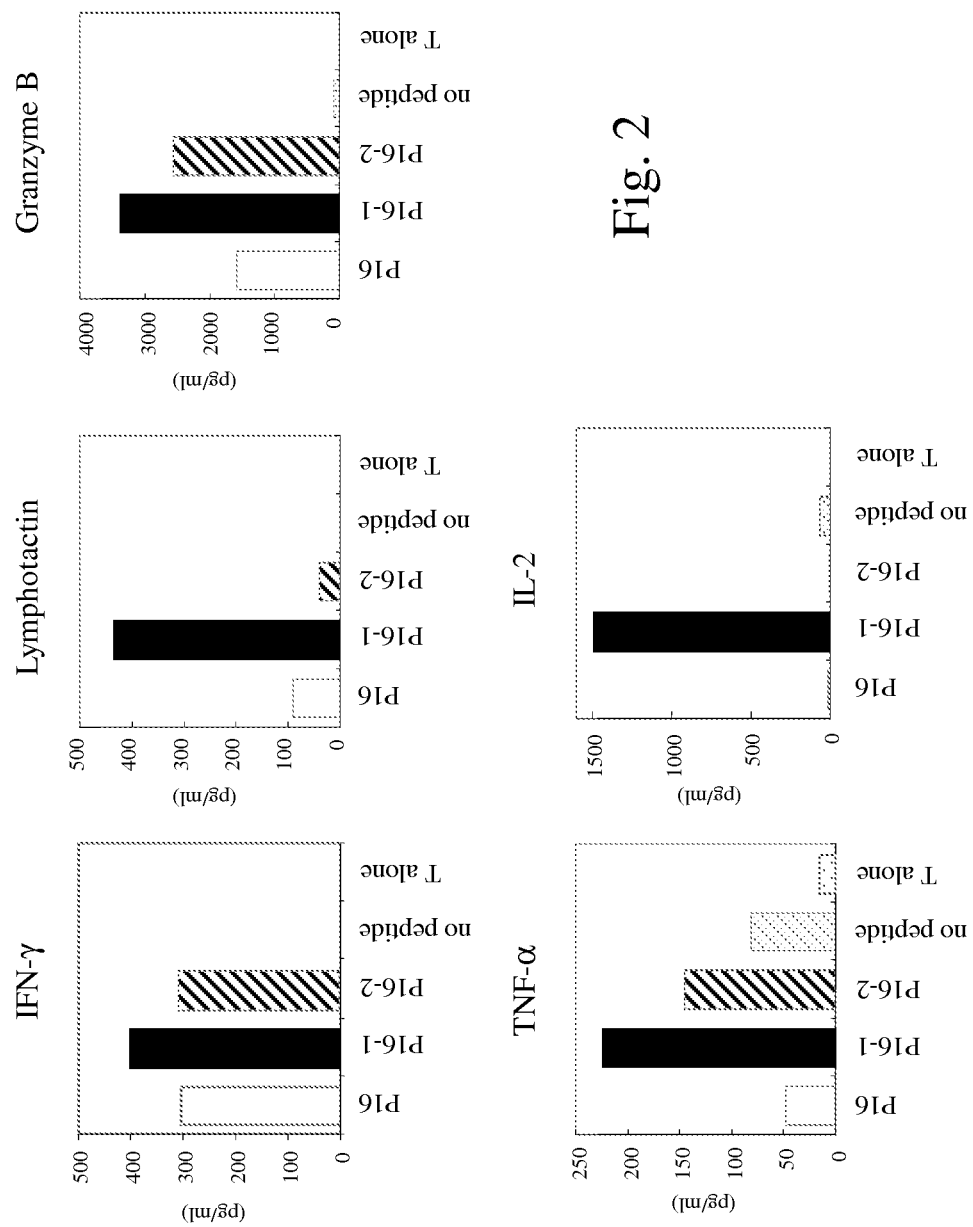
FIG. 2 is a set for bar graphs illustrating the ability of autologous B cells pulsed with native and agonist P16 peptides to induce IFN-γ, Lymphotactin, Granzyme B, TNF-α and IL-2 production by T cell line derived from the native peptide (T-A-P16). T-A-P16 cells were used as effectors at in vitro stimulation (IVS-4). T cells were stimulated with irradiated autologous B cells pulsed with different PAGE4 analogues at a concentration of 12.5 ul/ml, and an effector-to-APC ratio of 1:3. Twenty-four-hour culture supernatants were collected and screened for the secretion of IFN-γ, Lymphotactin, Granzyme B, TNF-α and IL-2 using ELISA assay.

Studies were then undertaken to examine the ability of the P16, P16-1, P16-2 peptides to activate the T-A-P16 cells, which were generated with the P16 native peptide. As seen in FIG. 2, the higher levels of IFN-γ, lymphotactin, Granzyme B, TNF-α and IL-2 production were observed when T-A-P16 cells were stimulated with P16-1 peptide as compared with the native P16 or P16-2 peptide. The P16-1 agonist was thus chosen for further study.

Example 4

P16-1 Agonist Peptide was Activates T Cells to Lyse Peptide-pulsed Targets

To examine the ability of the P16 and P16-1 peptides to activate the PAGE4-specific T-cells, T-A-P16 cells were subsequently analyzed for the ability to lyse peptide-pulsed targets. As shown in Table 3, lysis of T2 cells pulsed with the P16-1 peptide was higher than lysis of T2 cells pulsed with the P16 peptide, at two different E:T cell ratios.

TABLE 3

Ability of the PAGE4-specific T-cell lines (T-A-P16, T-B-P16-1) to lyse peptide-pulsed targets

| | % lysis (±SD)* | | | |
|---|---|---|---|---|
| | T-A-P16 | | T-B-P16-1 | |
| Target | 30:1 | 15:1 | 30:1 | 15:1 |
| T2 | 5.1 (1.1) | 6.4 (0.2) | 7.6 (0.1) | 6.6 (0.9) |
| T2 + P16 | 12.7 (1.7) | 9.1 (0.9) | 23.5 (0.6) | 22.7 (0.8) |
| T2 + P16-1 | 20.4 (1.9) | 16.7 (0.9) | 34.7 (0.04) | 25.8 (0.6) |

*A 16-hour $^{111}$In release assay was performed. Results are expressed in percent specific lysis at effector-to-target ratio of 30:1 and 15:1. Labeled T2 cells were incubated with or without peptide (12.5 µg/ml) in serum-free medium for 2 hours at 37° C. prior to their addition into the assay. Effector cells were used at IVS4.

As determined by flow cytometric analysis, the T-A-P16-1 cell line was 91.0% CD8 positive, 20.3% CD45RA positive, 11.2% CD28 positive, and 14.9% CD27 positive, 24.9% CCR7 positive.

To further characterize the P16-1 peptide, an additional T-cell line was established from another HLA-A2 positive prostate cancer patient (patient B) using P16-1 agonist peptide-pulsed autologous DCs. This T-cell line was designated T-B-P16-1. As determined by flow cytometric analysis, the T-B-P16-1 cell lines was 98.9% CD8 positive, <1% CD56 positive, 11.5% CD45RA positive, and 0.1% CD27 positive. As shown in table 3, T-B-P16-1 cells also lysed T2 cells pulsed with the P16-1 peptide to a greater extent than those pulsed with the P16 peptide, at two different E:T cell ratios. This result also supported that the modification of native to agonist peptide did not adversely affect the ability of the P16-1-induced CTLs to recognize the native epitope.

Figure 3:
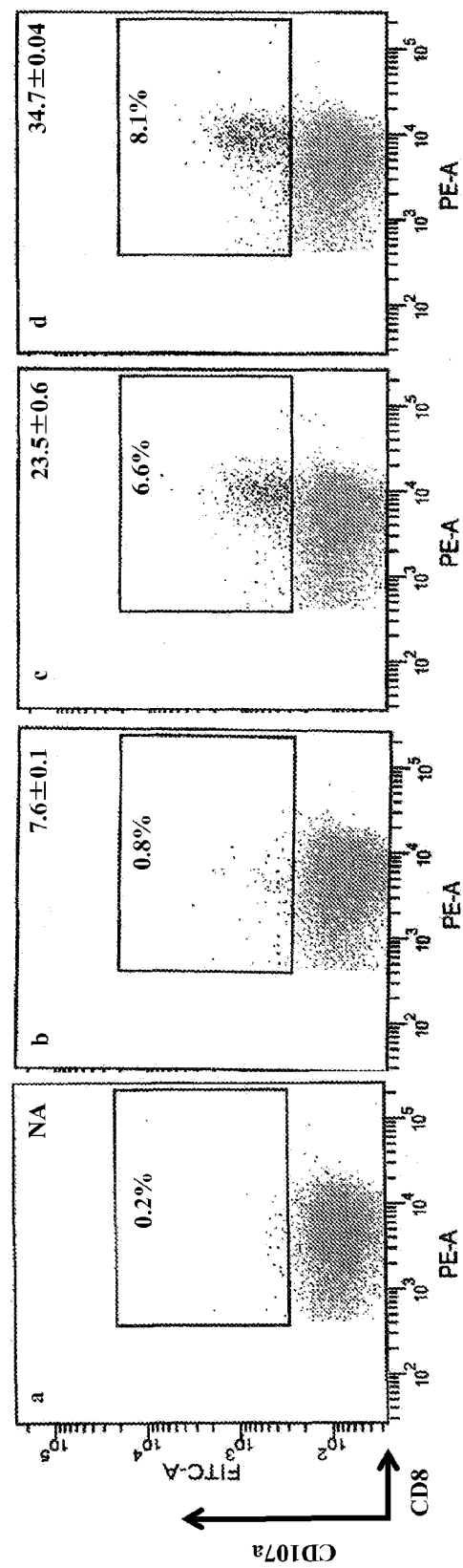
FIGS. 3a-3d are plots from T cell activation experiments analyzed by flow cytometry showing P16-1 agonist peptide is more effective to activate T cells to lyse peptide-pulsed targets than P16 native peptide as well as to generate T cell lines. The expression of CD107a on the cell surface of CD8+ T cells and correlation with cytotoxic activity by PAGE4-specific T-cell line (T-B-P16-1) against P16-1 or P16 pulsed T2 cells. $0.5 \times 10^6$ effector cells/ml were incubated (FIG. 3a) alone, (FIG. 3b) with T2 cells without peptide, (FIG. 3c) with T2 cells pulsed with 12.5 µg/ml of P16 peptide, or (FIG. 3d) with T2 cells pulsed with 12.5 µg/ml of P16-1 peptide. Results are expressed in % of CD107a positive and CD8 positive cells. Numbers of the upper right are % of specific lysis±SD.

In order to determine CTL degranulation which is a requisite process of perforin-granzyme mediated killing by activated CD8+ T cells, CD107a mobilization to the cell surface of CD8+ T cells was examined following activation with P16 or P16-1 peptides in addition to CTL assays. T-B-P16-1 cells were incubated with P16 native or P16-1 agonist peptide-pulsed T2 cells for 5 hours in the presence of monensin and analyzed for CD107a mobilization by flow cytometric analysis (FIG. 3). Higher number of CD8+ T cells expressed surface CD107a when the T-B-P16-1 cells were stimulated with the P16-1 peptide pulsed T2 cells as compared with the P16 native peptide pulsed T2 cells. Thus, these results showed a correlation between CD107a expression and cytotoxic activity by PAGE4-specific T-cell line (FIG. 3).

Example 5

CD8+CTLs Generated with P16-1 Agonist Peptide Kill PAGE4 Expressing Tumor Cells

Figure 4:
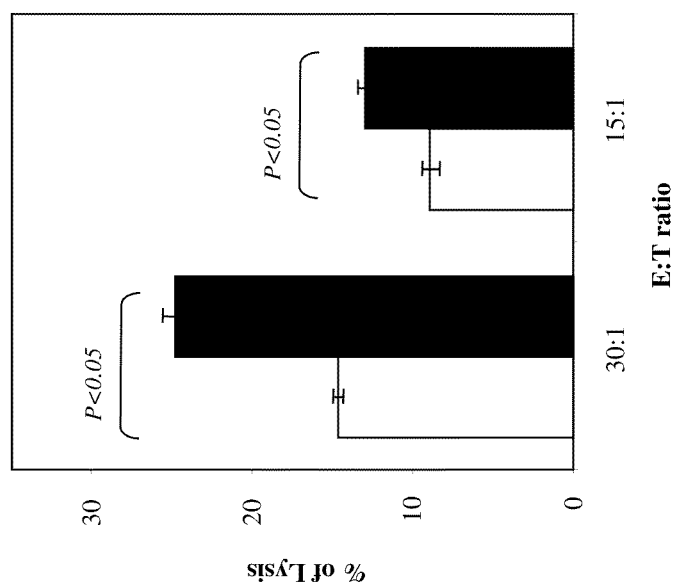
FIG. 4 is a bar graph showing the cytotoxicity of a PAGE4 specific T-cell line (T-A-P16, T-A-P16-1) against native PAGE4 and HLA-A2 expressing tumor cells. Cytotoxicity of T-A-P16 (open bar) and T-A-P16-1 (solid bar) against LNCaP cells with endogenous PAGE4 expression. A 16-hour $^{111}$In release assay was performed. Results are expressed in percent specific lysis at effector-to-target ratio of 30:1 and 15:1. Bars=SD. Statistically significant (P<0.05, two tailed t test). The results demonstrated that T-A-P16-1 has increased efficacy.

Studies were then conducted to determine whether the PAGE4-specific T-cell lines could lyse tumor cells that endogenously express native PAGE4. The expression of HLA-A2 and PAGE4 on tumor cell lines was analyzed by flow cytometry and RT-PCR, respectively (Table 4). As shown in FIG. 4, T-A-P16 cells were capable of lysing LNCaP human prostate cancer cells that express native PAGE4 and are HLA-A2 positive. Moreover, T-A-P16-1 cells established by using the P16-1 peptide lysed LNCaP cells to a greater extent than the T-A-P16 cells at two different E:T cell ratios.

TABLE 4

Tumor cells endogenously process PAGE4 to present PAGE4 peptide in the context of HLA-A2 for T-cell-mediated lysis.

Experiment 1: Ability of the PAGE4-specific T cell line to lyse human tumor cells expressing PAGE4

| Target | Type of cancer | HLA-A2 $^a$ | PAGE4 $^b$ | % Lysis (±SD) $^c$ |
|---|---|---|---|---|
| LNCaP | prostate cancer cells | 46.7 (19) | + | 20.4 (0.3) $^d$ |
| PC3/PAGE4 | prostate cancer cells | negative | + | 0.0 (0.0) |
| 22Rv1 | prostate cancer cells | negative | + | 0.0 (1.5) |
| MCF-7 | breast cancer cells | 97.7 (117) | − | 0.6 (1.0) |
| AsPC-1 | pancreatic cancer cells | negative | − | 0.0 (0.3) |

Experiment 2: Demonstration of HLA-A2 involvement

| Target | Infection | HLA-A2 $^a$ | PAGE4 $^b$ | % Lysis (±SD) $^c$ |
|---|---|---|---|---|
| 22Rv1 | uninfection | negative | + | 0.8 (0.3) |
| | V-WT | negative | + | 0.0 (1.0) |
| | rV-HLA-A2 | 61.4 (23) | + | 31.2 (1.9) $^e$ |
| MCF-7 | uninfection | 97.8 (43) | − | 0.6 (1.0) |
| | control plasmid | 95.5 (35) | − | 2.7 (0.9) |
| | pPAGE4 | 97.0 (37) | + | 43.8 (2.6) $^e$ |

$^a$ HLA-A2 expression was tested by flow cytometry. Results are expressed in percentage of positive cells (mean fluorescence intensity).
$^b$ PAGE4 mRNA expression was detected by reverse transcription-PCR.
$^c$ A 6-hour $^{111}$In release assay was performed using T-B-P16-1 cells. Results are expressed in percent specific lysis at effector-to-target ratio of 30:1 (Experiment 1) or 50:1 (Experiment 2).
$^d$ Statistical significance when comparing lysis of LNCaP cells versus PC3/PAGE4 cells, 22Rv1 cells, MCF-7 cells or AsPC-1 cells (P < 0.01, two tailed t test).
$^e$ Statistically significant lysis compared with V-WT infected and uninfected 22Rv1 cells as well as control plasmid infected and uninfected MCF-7 cells (P < 0.01, two tailed t test).

Since only 46.7% of cells expressed HLA-A2 molecules on the cell surface, the actual percentage of specific lysis for HLA-A2 expressing LNCaP cells could be normalized at 43.6%. Phenotype analysis of T-A-P16 and T-A-P16-1 cell lines showed that T-A-P16 cells were 97.3% CD8 positive, 12.3% CD45RA positive, 0.4% CD27 positive, and 21.6% CCR7 positive, and T-A-P16-1 cells were 99.5% CD8 positive, 13.5% CD45RA positive, 0.9% CD27 positive, and 24.9% CCR7 positive. To examine the frequency of PAGE4-specific CD8+ T cells in these cell lines, T cells were stained with PAGE4-P16-1/HLA-A*0201 tetramer and anti-CD8 antibodies. The results showed that 7.6% of T-A-P16 cells and 17.1% of T-A-P16-1 cells were tetramer-positive CD8+ T cells. These results indicated that P16-1 agonist peptide was more effective in generating CD8+ T cells with a high frequency of PAGE4 peptide than P16 native peptide. Low levels of lysis by T-A-P16 cells may be explained by the fact that T-A-P16-1 cells had a high number of PAGE4-specific T cells as mediated by tetramer binding assay.

Example 6

Tumor Cells Endogenously Process PAGE4 to Present PAGE4 Peptide in the Context of HLA-A2

As shown in Table 4, the T-B-P16-1 cells were only capable of lysing the LNCaP cells (PAGE4 positive, HLA-A2 positive), but showed no lysis against the HLA-A2-negative PC3 human prostate cancer cells transfected with the human PAGE4 gene (PC3/PAGE4), 22Rv1 human prostate cancer cells (PAGE4 positive, HLA-A2 negative), MCF-7 human breast cancer cells (PAGE4 negative, HLA-A2 positive), AsPC-1 human pancreatic cancer cells (PAGE4 negative, HLA-A2 negative).

To confirm the hypothesis that human tumors endogenously processed the entire PAGE4 molecule in a manner so as to bind HLA-A2 molecules for presentation at the cell surface. 22Rv1 cells (PAGE4 positive, HLA-A2 negative) were transfected with rV-HLA-A2 recombinant and used as target cells in a T-cell cytotoxic assay. As shown in Table 4, 22Rv1 cells expressed HLA-A2 after infection with rV-HLA-A2. 22Rv1 cells were susceptible to lysis with T-B-P16-1 cells when transfected with rV-HLA-A2 but not with control V-WT. In addition, MCF-7 cells (PAGE4 negative, HLA-A2 positive) were transfected with the human PAGE4 gene and used as target cells in a T-cell cytotoxic assay. As shown in Table 4, MCF-7 cells were susceptible to lysis with T-B-P16-1 cells when transfected with pPAGE4 but not with control plasmid. These results support the hypothesis that human tumors endogenously processed the entire PAGE4 molecule and the HLA-A2-restricted nature of the PAGE4 specific lysis of the T-B-P16-1 cells.

Figure 5:
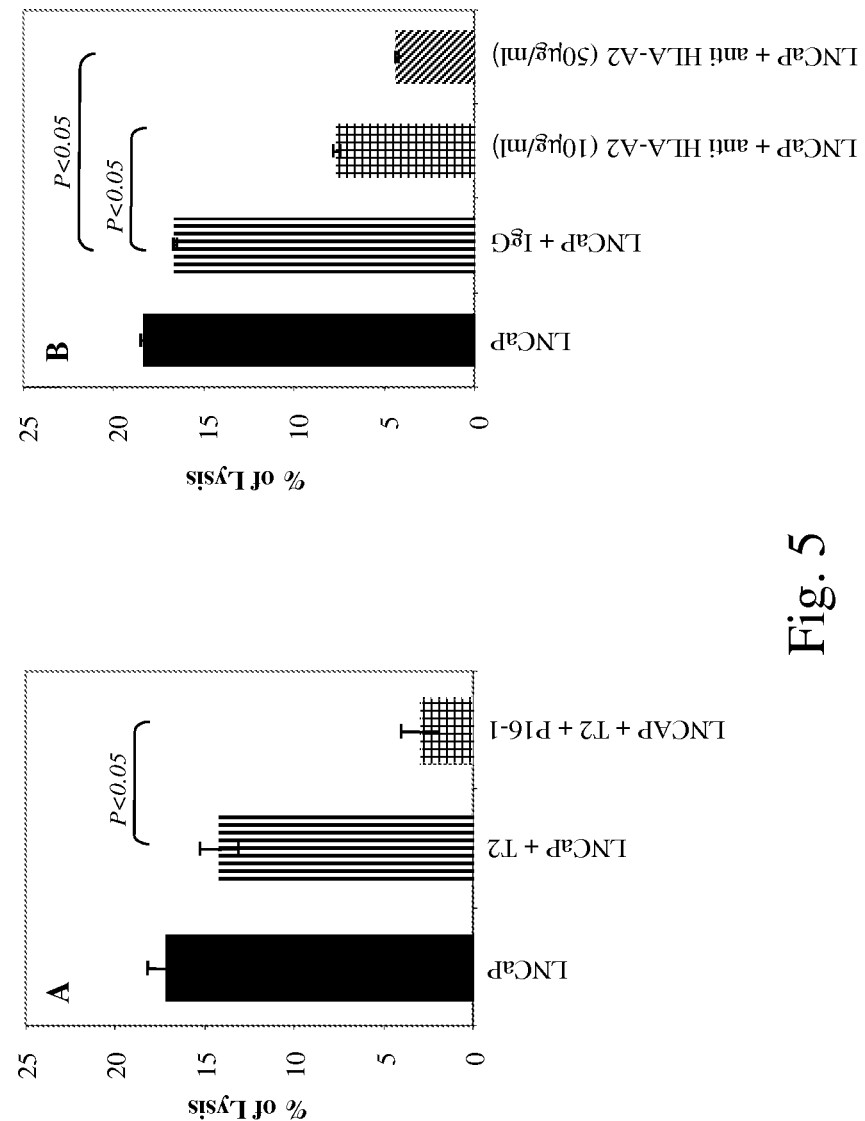
FIGS. 5A-5B are bar graphs showing the cytotoxicity of a PAGE4 specific T-cell line (T-A-P16-1) against target cells with endogenous PAGE4 expression and inhibition of lysis by cold target inhibition or anti-HLA-A2 antibody. For the results presented in FIG. 5A, $^{111}$In labeled LNCaP cells and unlabeled T2 cells were used at a ratio of 1:10. T2 cells were incubated with or without P16-1 peptide (12.5 µg/ml) in serum-free medium for 2 hours at 37° C. prior to the addition of the T-A-P16-1 cells. For the results presented in FIG. 5B, anti-HLA-A2 antibody (10 µg/ml and 50 µg/ml) or 10 µg/ml of control IgG antibody were added to $^{111}$In labeled LNCaP cells for 1 hour at 37° C. prior to the addition of the T-A-P16-1 cells. Results are expressed in percent specific lysis at effector-to-target ratio of 15:1. Bars=SD. Statistically significant (P<0.05, two tailed t test).

To confirm the specificity and HLA-A2 restriction of CTL cytolysis, LNCaP cells were used as target in a cold target inhibition assay. As shown in FIG. 5A, the addition of P16-1 agonist peptide-pulsed unlabeled T2 cells decreased 79.6% in the CTL activity of T-A-P16-1 cells against labeled LNCaP cells. Moreover, to determine whether the lysis was HLA-A2 restricted, antibody blocking experiments were carried out. The CTL activity of T-A-P16-1 cells against LNCaP cells was shown to be HLA-A2 restricted as indicated by the inhibition of lysis with anti-HLA-A2 antibody but not with control antibody (FIG. 5B). These results showed that PAGE4-specific T-cells generated using the agonist P16-1 could lyse tumor cells that endogenously express native PAGE4 in an antigen specific and HLA-A2 restricted manner.

Example 7

Figure 6A:
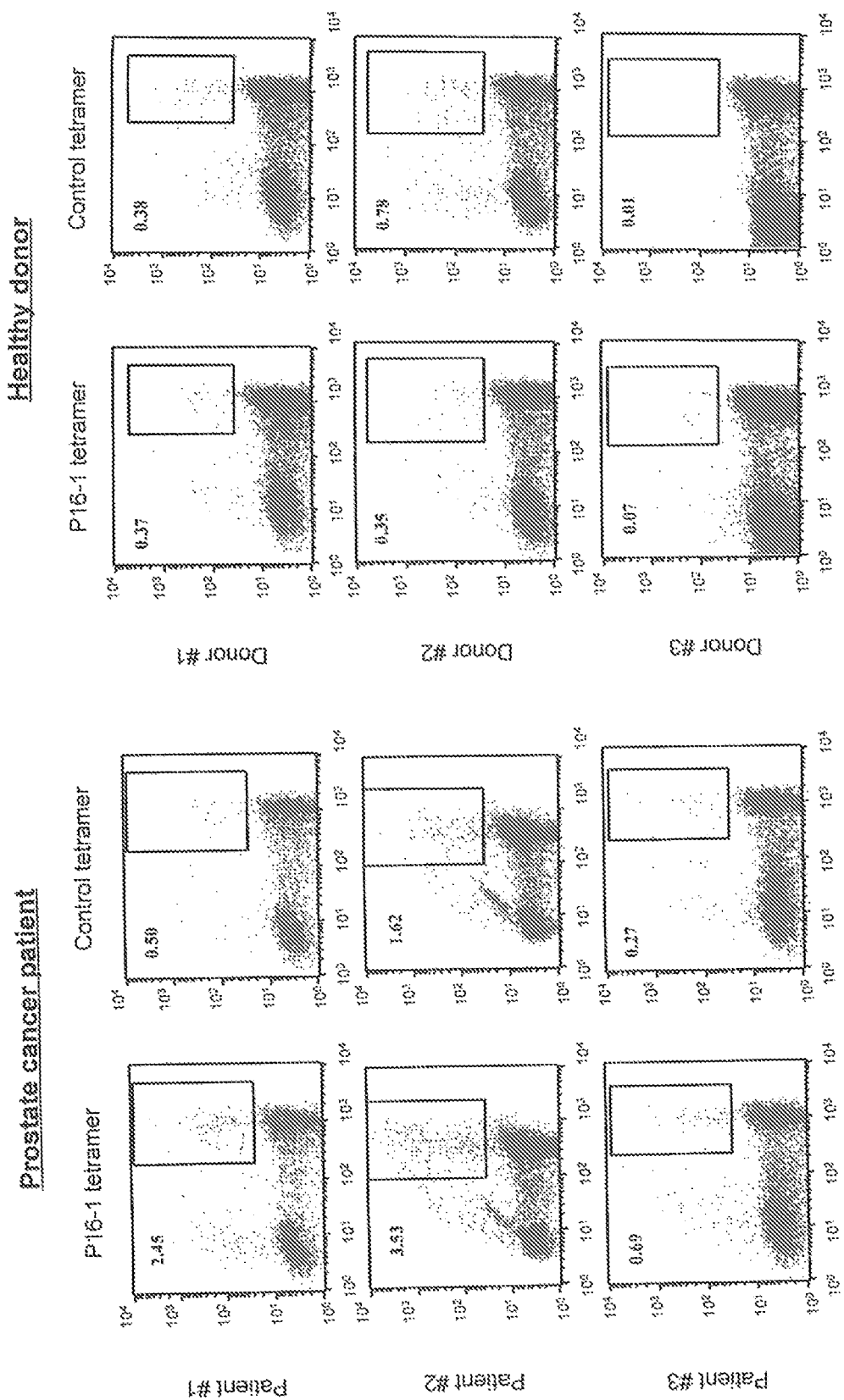
FIGS. 6A-6B are a set of plots showing the identification of PAGE4-P16-1 specific CD8+ T cells in prostate cancer patients. PE-labeled PAGE4-P16-1/HLA-A*0201 tetramer or control tetramer PE-labeled HIV gag/HLA-A*0201 tetramer was used. $5 \times 10^5$ T cells were stained with 10 µl of tetramers and anti-CD8 antibody for 30 minutes at room temperature protected from light. For the results presented in FIG>6A, after one in vitro stimulation (IVS) with autologous DCs pulsed with P16-1 peptide, PBMC from prostate cancer patients (patients #1-#3) or PBMC from healthy donors (donors #1-#3) were tested concurrently. $1 \times 10^5$ cells were acquired on a FACSCALIBUR™ flow cytometer (BD Biosciences) and data were analyzed using CELL QUEST™ software (BD Biosciences). For the results presented in FIG. 6B, after two IVS with autologous DCs pulsed with P16-1 peptide, PBMC from prostate cancer patients (patients #4 and #5) or PBMC from healthy donors (donors #4 and #5) were tested. $1 \times 10^5$ cells were acquired on a LSRII (BD Biosciences) and data were analyzed using FLOWJO™ software (BD Biosciences). Results are expressed in percentage of tetramer positive and CD8 positive cells.
Figure 6B:
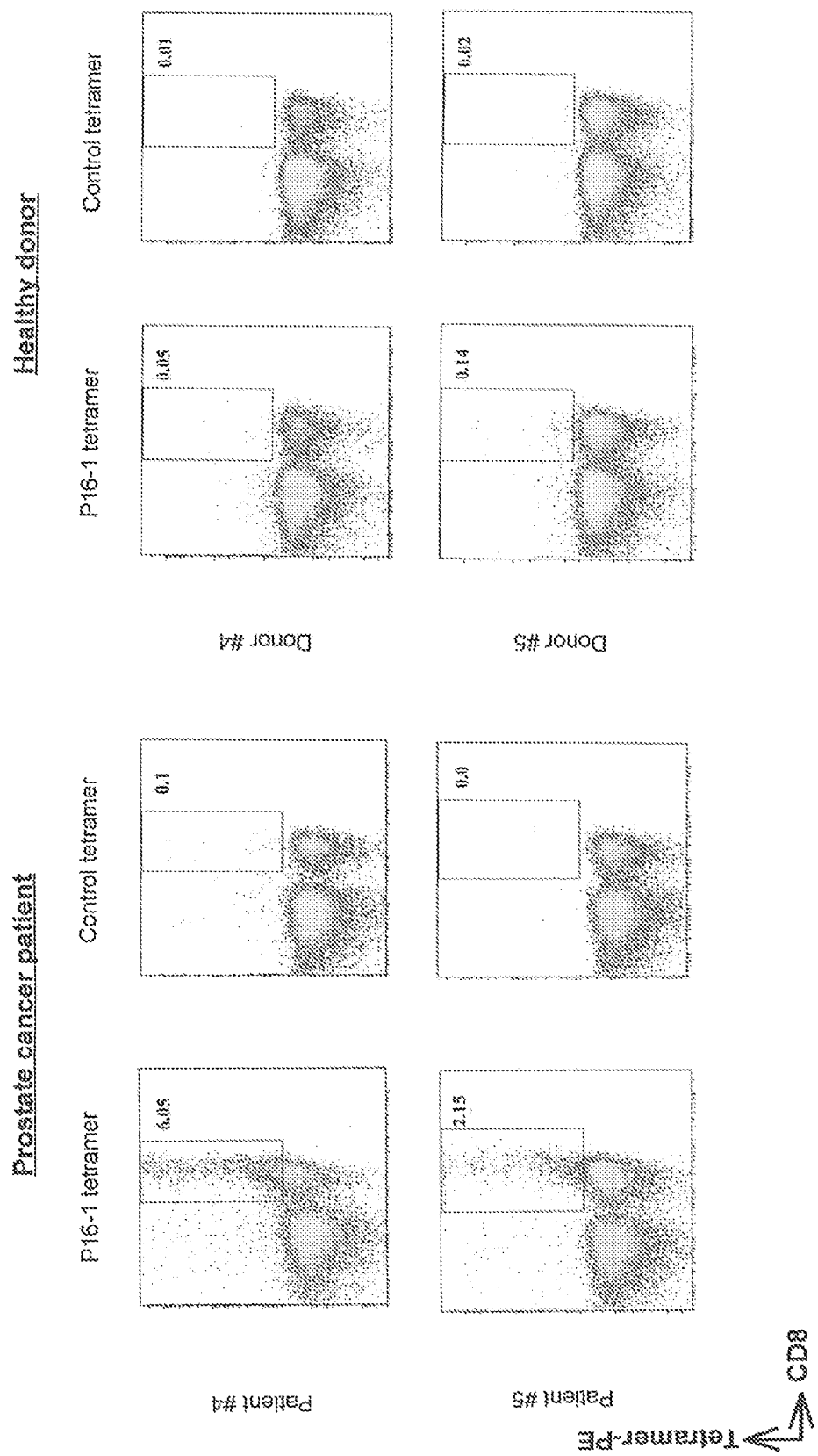

Identification of P16-1 Specific T Cells in Healthy Individuals and Prostate Cancer Patients To evaluate the potential of PAGE4 epitope P16-1 for vaccine mediated immunotherapy, we investigated whether P16-1 specific T cells could be identified from PBMC of healthy individuals and prostate cancer patients. To compare the frequency and phenotype of P16-1 specific T cells in healthy individuals and prostate cancer patients, PE-labeled PAGE4-P16-1/HLA-A*0201 tetramer was used to identify the P16-1 specific T cells. T cells were cultured in vitro for one IVS (FIG. 6A) or two IVS (FIG. 6B) prior to tetramer staining. The frequency of PAGE4-P16-1/HLA-A*0201 tetramer positive cells in $CD8^+$ T cells was higher in prostate cancer patients as compared to healthy individuals in both WS-1 and IVS-2 cultures These results suggest that the PAGE4 agonist peptide P16-1 can be used alone or in combination with other peptides of prostate cancer associated antigens in sensitive immunoassays to monitor immune responses of patients in prostate cancer vaccine clinical trials.

PAGE4 is a CT antigen that expressed in hormone-dependent and hormone-refractory prostate cancers as well as in uterine cancers. It is also found in prostate cancer cell lines such as LNCaP cells (Prikler et al., Aktuel Urol 2004; 35:326-330). This study identifies PAGE4-derived HLA-A2-restricted CTL epitopes and modification of the primary anchor residues of the novel PAGE4 peptides, shown to enhance the binding affinity to HLA-A2 molecule. Four analogues were synthesized and analyzed.

The results of this study show the enhanced synthesis of IFN-γ, TNF-α, IL-2, Granzyme B and chemokine Lymphotactin as a consequence of stimulation of PAGE4 specific T cells with the agonist P16-1 peptide. Preclinical and clinical studies have indicated that lymphotactin may be an important chemokine in attracting effector cells and thus enhancing immune responses.

Degranulation is a requisite process of perforin-granzyme mediated killing, and is a critical step required for immediate lytic function mediated by responding antigen-specific CD8+ T cells. The lytic granules are membrane-bound secretory lysosomes that contain a dense core composed of various proteins, including perforin and granzymes. It is possible to directly estimate the degranulation in primary responding antigen-specific CD8+ T cells by measuring the cumulative exposure of granular membrane proteins (CD107a and b) on the cell surface (Rubio et al, Nat Med 2003; 9:1377-82). In the present study, PAGE4-specific CD8+ T cells stimulated with PAGE4 peptides increased surface mobilization of CD107a, and showed the correlation between CD107a mobilization to the cell surface and cytotoxic activity. More importantly, T cells stimulated by the agonist peptide P16-1 showed higher levels of CD107a on the cell surface as compared with T cells stimulated with the native peptide P16.

T-cell lines derived from prostate cancer patients using the native or the agonist PAGE4 epitopes were shown to lyse PAGE4 positive and HLA-A2 positive prostate cancer cell lines, as well as PAGE4 gene-transfected MCF-7 cells in an MHC-restricted manner. The studies thus indicate that the PAGE4 agonist peptide could be used (alone or in combination with other peptides of prostate cancer associated antigens) to produce sensitive immunoassays to monitor immune responses of patients involved in prostate cancer vaccine clinical trials.

Preclinical studies have shown that the use of poxvirus recombinant vectors encoding the transgenes for CEA and a triad of T-cell costimulatory molecules (B7-1, ICAM-1 and LFA-3) (TRICOM) results in far greater activation of antigen-specific CD4 and CD8 T cells and antitumor activity (Hodge et al., Cancer Res 1999; 59:5800-7; Hodge et al., J Natl Cancer Inst 2000; 92:1228-1239; Hodge J W, et al., Vaccine 2001; 19:3552-67; Zhu et al., Cancer Res 2001; 61:3725-34; Tsang et al., Clin Cancer Res 2005; 11:1597-1607). Several clinical trials involving poxvirus recombinant vectors encoding the transgenes for PSA, MUC-1 or CEA containing the agonist epitopes and TRICOM are in progress in cancer patients (Gulley et al., Abstr Am Soc Clin Oncol. Prostate Cancer Sympium 2005; 1:Abs 256).

These PAGE4 epitopes, such as P16 and P16-1 are the first CTL epitopes to be identified for PAGE4. The PAGE4 polypeptide disclosed herein could be used as a peptide vaccine in adjuvant or in autologous peptide-pulsed DC therapy for prostate cancer. PAGE4 transgene with agonist epitope can be used as part of the recombinant viral vectors for the treatment of prostate cancer.

Example 8

Administration of PAGE4 in Conjunction a Co-Stimulatory Molecule

The origin of vaccinia parental virus is the New York City Board of Health strain and was obtained by Wyeth from the New York City Board of Health and passaged in calves to create the Smallpox Vaccine Seed. Flow Laboratories received a lyophilized vial of the Smallpox Vaccine Seed, Lot 3197, Passage 28 from Drs. Chanock and Moss (National Institutes of Health). This seed virus was ether-treated and plaque-purified three times.

For the generation of rV-TRICOM(mu1), a plasmid vector, designated pT5032 was constructed to direct insertion of the foreign sequences into the M2L (30K) gene, which is located in the Hind III M region of the vaccinia genome. The murine LFA-3 gene is under the transcriptional control of the vaccinia 30K (M2L) promoter, the murine ICAM-1 gene is under the control of the vaccinia I3 promoter, and the murine B7-1 gene is under the control of the synthetic early/late (sE/L) promoter. These foreign sequences are flanked by DNA sequences from the Hind III M region of the vaccinia genome (see FIG. 1 of U.S. Patent Application Publication No. 2004/0019195, incorporated herein by reference). These flanking sequences include the vaccinia K1L host range gene.

A derivative of the Wyeth strain of vaccinia was used as the parental virus in the construction of recombinant vaccinia virus. This parental virus, designated vTBC33, lacks a functional K1L gene and thus cannot efficiently replicate on rabbit kidney RK13 cells. The generation of recombinant vaccinia virus was accomplished via homologous recombination between vaccinia sequences in the vTBC33 vaccinia genome and the corresponding sequences in pT5032 in vaccinia-infected RK13 cells transfected with pT5032. Recombinant virus, designated vT171, was selected by growth on RK13 cells (ATCC Accession No. CCL 37). Plaques were picked from the cell monolayer and their progeny were further propagated. Two rounds of plaque isolation and replating on RK13 cells resulted in the purification of the desired recombinant.

For the generation of rV-PAGE4/TRICOM(mu), a plasmid vector, designated pTXXXX, was constructed to direct insertion of the foreign sequences into the M2L (30K) gene, which is located in the Hind III M region of the vaccinia genome. The nucleic acid encoding an immunogenic PAGE4 polypeptide is under the control of the 40K promoter, the murine LFA-3 gene is under the control of the 30K promoter, the murine ICAM-1 gene is under the control of the I3 promoter, and the murine B7-1 gene is under the control of the sE/L promoter.

These foreign sequences are flanked by DNA sequences from the Hind III M region of the vaccinia genome, including the vaccinia K1L host range gene. vTBC33, described above, is used as the parental virus in the construction of the recombinant vaccinia virus. The generation of recombinant vaccinia virus is accomplished via homologous recombination between vaccinia sequences in the vTBC33 vaccinia genome and the corresponding sequences in pTXXX in vaccinia-infected RK.sub.13 cells transfected with pT5031. Recombinant virus, designated vTXXX, was selected by growth on RK13 cells as described above. Plaques were picked from the cell monolayer and their progeny were further propagated. Two rounds of plaque isolation and replating on RK13 cells resulted in the purification of the desired recombinant.

The individual recombinant vaccinia viruses containing either the gene encoding murine costimulatory molecule B7-1 (designated rV-B7-1) or the gene encoding murine Intercellular adhesion molecule-1 (designated rV-ICAM-1) have been described. The recombinant vaccinia virus containing the gene for murine CD48 [designated rV-LFA-3; murine CD48 is the homologue of human LFA-3 (CD58)] was constructed in a similar fashion to rV-B7-1 and rV-ICAM-1, and has been described. In each of these single recombinant vaccinia viruses, the gene encoding the costimulatory molecule was put under the control of the vaccinia virus early/late 40K promoter, and the transgene was inserted into the Hind III M region of the genome of the Wyeth strain of vaccinia virus.

Recombinant fowlpox viruses were constructed by the insertion of foreign sequences into the BamHI J region of the genome of the POXVAC-TC (Schering Corporation) strain of fowlpox virus as described. In recombinant viruses containing a single foreign gene, the gene is under control of the vaccinia 40K promoter. rV-B7-1/ICAM-1 is a recombinant vaccinia virus that contains the murine B7-1 gene under control of the synthetic early/late (sE/L) promoter and the murine ICAM-1 gene under control of the 40K promoter. rV-B7-1/ICAM-1/LFA-3 is a recombinant vaccinia virus that contains the murine LFA-3 gene under control of the vaccinia 30K (M2L) promoter, the murine ICAM-1 gene under control of the vaccinia I3 promoter, and the murine B7-1 gene under control of the synthetic early/late (sE/L) promoter.

rF-PAGE4/B7-1/ICAM-1/LFA-3 is a recombinant fowlpox virus that contains a nucleic acid encoding an immunostimulatory PAGE4 polypeptide, such as P16-1, under control of the 40K promoter, the murine B7-1 gene under control of the sE/L promoter, the murine LFA-3 gene under control of the I3 promoter, and the murine ICAM-1 gene under control of the vaccinia 7.5K promoter (see U.S. Patent Publication No. 2004/0019195, which is incorporated herein by reference).

To confirm that each of the recombinant vectors could express the appropriate transgene(s), the murine adenocarcinoma cell line MC38 are infected with the recombinant vaccinia construct, and cell-surface expression of the transgene(s) is demonstrated by flow cytometry. Uninfected cells and cells infected with wild-type vaccinia failed to express any of the three costimulatory molecules.

It will be apparent that the precise details of the methods or compositions described may be varied or modified without departing from the spirit of the described invention. We claim all such modifications and variations that fall within the scope and spirit of the claims below.

The invention claimed is:

1. A method of treating a subject with a PAGE4-expressing cancer, comprising administering to the subject a therapeutically effective amount of a polypeptide, or a therapeutically effective amount of a vector comprising a nucleic acid encoding the polypeptide,
  wherein the amino acid sequence of the polypeptide consist of amino acids 16 to 25 of SEQ ID NO: 1, ($X_1X_2$APDVVAFV), wherein amino acid $X_1$ is a glutamine or a tryrosine and amino acid $X_2$ is a glutamic acid or a lecuine, and wherein the vector does not encode the amino acid sequence set forth as SEQ ID NO: 1,
  thereby treating the PAGE4-expressing cancer in the subject.

2. The method of claim 1, wherein the amino acid sequence polypeptide consists of one of:
  (a) amino acids 16 to 25 of SEQ ID NO: 1, wherein amino acid $X_1$ is a glutamine and amino acid $X_2$ is a leucine,
  (b) amino acid 16 to 25 of SEQ ID NO: 1, wherein amino acid $X_1$ is a tyrosine and amino acid $X_2$ is a leucine.

3. The method of claim 2, wherein the amino acid sequence of the polypeptide consists of amino acids 16 to 25 of SEQ ID NO: 1, wherein amino acid $X_1$ is a glutamine and amino acid $X_2$ is a leucine.

4. The method of claim 2, wherein the amino acid sequence of the polypeptide consists of amino acids 16 to 25 of SEQ ID NO: 1, wherein amino acid $X_1$ is a tyrosine and amino acid $X_2$ is a leucine.

5. The method of claim 1, comprising administering to the subject a therapeutically effective amount of the vector encoding the polypeptide, wherein the vector is a plasmid, yeast, retrovirus, orthopox, avipox, fowlpox, capripox, suipox, adenoviral, herpes virus, alpha virus, baculovirus, Sindbis virus, vaccinia virus or poliovirus vector.

6. The method of claim 1, comprising administering to the subject a therapeutically effective amount of the vector encoding the polypeptide, wherein the vector is a first recombinant virus which has incorporated into a viral genome the polynucleotide encoding the isolated polypeptide, and wherein the method further comprises administering to the subject a therapeutically effective amount of a second recombinant virus which has incorporated into a viral genome thereof one or more genes or DNA sequences encoding a costimulatory molecule.

7. The method of claim 6, wherein the costimulatory molecule is one or more of B7-1, B7-2, LFA or ICAM-1.

8. The method of claim 6, wherein the first recombinant virus, the second recombinant virus, or the first and second recombinant viruses is selected from the group consisting of retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors.

9. The method of claim 6, wherein the first recombinant virus, the second recombinant virus, or the first and second recombinant virus is vaccinia or fowl pox virus.

10. The method of claim 6, wherein the second recombinant virus further comprises one or more exogenous DNA sequences encoding one or more immunostimulatory molecules, wherein the immunostimulatory molecule is selected from the group consisting of IL-2, ICAM-1, LFA-3, CD72, GM-CSF, TNF-α, IFN-γ, IL-12, and IL-6.

11. The method of claim 1, further comprising administering to the subject a therapeutically effective amount of one or more exogenous immunostimulatory molecules, wherein the immunostimulatory molecules are selected from the group consisting of IL-2, IL-12, RANTES, GM-CSF, TNF-α, IFN-γ, IFN-α, IL-15, and G-CSF, or administering to the subject a combination more than one of the exogenous immunostimulatory molecules.

12. The method of claim 1, further comprising administering to the subject a therapeutically effective amount of a nucleic acid encoding one or more of IL-2, RANTES, GM-CSF, TNF-α, IFN-γ, IFN-α, IL-15, G-CSF, LFA-3, CD72, B7-1, B7-2, OX-40L, 41 BBL and ICAM-1.

13. A polypeptide consisting of
  amino acids 59 to 68 of SEQ ID NO: 1($X_3X_4$GDCQEMD$X_5$), wherein amino acid $X_3$ is a valine, amino acid $X_4$ is a glutamic acid, and amino acid $X_5$ is a valine.

14. An isolated polynucleotide comprising a nucleic acid sequence encoding the polypeptide of claim 13.

15. A vector comprising the polynucleotide of claim 14.

16. A plasmid or viral vector encoding a polypeptide
  consisting of amino acids 59 to 68 SEQ ID NO: 1($X_3X_4$GDCQEMD$X_5$), wherein amino acid $X_3$ is a valine, amino acid $X_4$ is a glutamic acid, and amino acid $X_5$ is a valine, and wherein the plasmid or viral vector does not encode SEQ ID NO: 1.

17. The vector of claim 16, wherein the vector is a retrovirus, orthopox, avipox, fowlpox, capripox, suipox, adenoviral, herpes virus, alpha virus, baculovirus, Sindbis virus, vaccinia virus or a poliovirus viral vector.

18. A composition comprising a first recombinant virus which has incorporated into a viral genome a nucleic acid encoding the isolated polypeptide of claim 13 and a second recombinant virus which has incorporated into a viral genome thereof one or more genes or DNA sequences encoding a costimulatory molecule, wherein the composition is able to coinfect a host cell resulting in coexpression of the polypeptide and the encoding genes or DNA sequences encoding the costimulatory molecule.

19. The composition of claim 18, wherein the costimulatory molecule is one or more of B7-1, B7-2, LFA or ICAM-1.

20. The composition of claim 18, wherein the first recombinant virus, the second recombinant virus, or both the first and second recombinant viruses are selected from the group consisting of retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors.

21. The composition of claim 18, wherein the second recombinant virus further comprises one or more exogenous DNA sequences encoding one or more immunostimulatory molecules, wherein the immunostimulatory molecule is selected from the group consisting of IL-2, IL-12, ICAM-1, LFA-3, CD72, GM-CSF, INF-α, IFN-γ, and IL-6.

22. The composition of claim 21, wherein the composition further comprises an immunomodulating effective amount of at least one exogenous immunostimulatory molecule selected from the group consisting of IL-2, GM-CSF, TNF-α, IL-12, and IL-6, or wherein the composition further comprises an immunomodulating effective amount of a combination of the exogenous immunolstimulatory molecules.

23. The composition of claim 18, wherein the first recombinant virus, the second recombinant virus, or the first and second recombinant virus is vaccinia or fowlpox virus.

24. A pharmaceutical composition comprising the plasmid Or viral vector of claim 16, and a pharmaceutically acceptable carrier.

25. An isolated host cell transformed with the plasmid or viral vector of claim 16.

26. The isolated host cell of claim 25, wherein the host cell is a dendritic cell or a tumor cell.

27. A method for eliciting an immune response in a subject, comprising:
administering to a subject a therapeutically effective amount of the polypeptide of claim 13, or a polynucleotide encoding the polypeptide,
thereby producing an immune response to a polypeptide comprising the amino acid sequence set forth as SEQ ID NO: 1 in the subject.

28. The method of claim 27, further comprising administering an adjuvant to the subject.

29. The method of claim 27, further comprising administering to the subject a therapeutically effective amount of IL-2, IL-12, RANTES, GM-CSF, TNF-α, IFN-γ, G-CSF or a combination thereof.

30. The method of claim 27, further comprising administering to the subject a nucleic acid encoding one or more of IL-2, IL-12, RANTES, GM-CSF, TNF-α, IFN-γ, IFN-α, IL-15, G-CSF, LFA-3, CD72, B7-1, B7-2, OX-40L, 41 BBL and ICAM-1.

31. A method of enhancing an immune response against cells expressing PAGE4 in a mammal comprising:
infecting cells in vitro with a therapeutically effective amount of the vector of claim 16, wherein the vector is a viral vector, to produce infected cells expressing the immunogenic PAGE4 polypeptide and
administering an amount of infected cells to a mammal afflicted with cells expressing a PAGE4 protein, thereby enhancing the immune response.

32. The method of claim 31, wherein the cells in vitro are dendritic cells or tumor cells.

33. The method of claim 31, further comprising administering an adjuvant to the subject.

34. The method of claim 31, further comprising administering to the subject a therapeutically effective amount of IL-2, IL-12, RANTES, GM-CSF, TNF-α, IFN-γ, IFN-α, IL-15, G-CSF or a combination thereof.

35. The method of claim 31, further comprising administering to the subject an nucleic acid encoding one or more of IL-2, IL-12, RANTES, GM-CSF, TNF-α, IFN-γ, IFN-α, IL-15, G-CSF, LFA-3, CD72, B7-1, B7-2, OX-40L, 41 BBL and ICAM-1.

36. A method for inhibiting the growth of a cancer cell in vitro, the method comprising:
(i) culturing cytotoxic T lymphocytes (CTLs) or CTL precursor cells with the polypeptide of claim 13 and an antigen presenting cell to produce activated CTLs that recognize the cancer cells, and
(ii) contacting the cancer cell with the activated CTLs,
thereby inhibiting the growth of the cancer cell in vitro, wherein the cancer cell is a reproductive cancer cell.

* * * * *

SEQUENCE LISTING

<160> NUMBER OF SEQ ID NOS: 7

<210> SEQ ID NO 1
<211> LENGTH: 102
<212> TYPE: PRT
<213> ORGANISM: Homo sapiens

```
<220> FEATURE:
<221> NAME/KEY: MISC_FEATURE
<222> LOCATION: (16)..(16)
<223> OTHER INFORMATION: Xaa can be Gln or Tyr
<220> FEATURE:
<221> NAME/KEY: MISC_FEATURE
<222> LOCATION: (17)..(17)
<223> OTHER INFORMATION: Xaa can be Glu or Leu
<220> FEATURE:
<221> NAME/KEY: MISC_FEATURE
<222> LOCATION: (59)..(59)
<223> OTHER INFORMATION: Xaa can be Val or Tyr
<220> FEATURE:
<221> NAME/KEY: MISC_FEATURE
<222> LOCATION: (60)..(60)
<223> OTHER INFORMATION: Xaa can be Glu or Leu
<220> FEATURE:
<221> NAME/KEY: MISC_FEATURE
<222> LOCATION: (68)..(68)
<223> OTHER INFORMATION: Xaa can be Val or Leu
<220> FEATURE:
<221> NAME/KEY: MISC_FEATURE
<222> LOCATION: (84)..(84)
<223> OTHER INFORMATION: Xaa can be Lys or Tyr
<220> FEATURE:
<221> NAME/KEY: MISC_FEATURE
<222> LOCATION: (85)..(85)
<223> OTHER INFORMATION: Xaa can be Thr or Leu
<220> FEATURE:
<221> NAME/KEY: MISC_FEATURE
<222> LOCATION: (92)..(92)
<223> OTHER INFORMATION: Xaa can be Ala or Val

<400> SEQUENCE: 1

Met Ser Ala Arg Val Arg Ser Arg Ser Arg Gly Arg Gly Asp Gly Xaa
1               5                   10                  15

Xaa Ala Pro Asp Val Val Ala Phe Val Ala Pro Gly Glu Ser Gln Gln
                20                  25                  30

Glu Glu Pro Pro Thr Asp Asn Gln Asp Ile Glu Pro Gly Gln Glu Arg
            35                  40                  45

Glu Gly Thr Pro Pro Ile Glu Glu Arg Lys Xaa Xaa Gly Asp Cys Gln
        50                  55                  60

Glu Met Asp Xaa Glu Lys Thr Arg Ser Glu Arg Gly Asp Gly Ser Asp
65                  70                  75                  80

Val Lys Glu Xaa Xaa Pro Pro Asn Pro Lys His Xaa Lys Thr Lys Glu
                85                  90                  95

Ala Gly Asp Gly Gln Pro
            100

<210> SEQ ID NO 2
<211> LENGTH: 102
<212> TYPE: PRT
<213> ORGANISM: Homo sapiens

<400> SEQUENCE: 2

Met Ser Ala Arg Val Arg Ser Arg Ser Arg Gly Arg Gly Asp Gly Gln
1               5                   10                  15

Glu Ala Pro Asp Val Val Ala Phe Val Ala Pro Gly Glu Ser Gln Gln
                20                  25                  30

Glu Glu Pro Pro Thr Asp Asn Gln Asp Ile Glu Pro Gly Gln Glu Arg
            35                  40                  45

Glu Gly Thr Pro Pro Ile Glu Glu Arg Lys Val Glu Gly Asp Cys Gln
        50                  55                  60

Glu Met Asp Leu Glu Lys Thr Arg Ser Glu Arg Gly Asp Gly Ser Asp
65                  70                  75                  80
```

Val Lys Glu Lys Thr Pro Pro Asn Pro Lys His Ala Lys Thr Lys Glu
                85                  90                  95

Ala Gly Asp Gly Gln Pro
        100

<210> SEQ ID NO 3
<211> LENGTH: 491
<212> TYPE: DNA
<213> ORGANISM: Homo sapiens

<400> SEQUENCE: 3
ggtcgacctt cgccaggctc tctgctgact caagttcttc agttcacgat cttctagttg     60
cagcgatgag tgcacgagtg agatcaagat ccagaggaag aggagatggt caggaggctc    120
ccgatgtggt tgcattcgtg gctcccggtg aatctcagca agaggaacca ccaactgaca    180
atcaggatat tgaacctgga caagagagag aaggaacacc tccgatcgaa gaacgtaaag    240
tagaaggtga ttgccaggaa atggatctgg aaaagactcg gagtgagcgt ggagatggct    300
ctgatgtaaa agagaagact ccacctaatc ctaagcatgc taagactaaa gaagcaggag    360
atgggcagcc ataagttaaa aagaagacaa gctgaagcta cacacatggc tgatgtcaca    420
ttggaaatgt gactgaaaat ttggaaattc tctcaataga gtctgagttt ctctctgaaga   480 aaaaaaaaaa a                                                         491

<210> SEQ ID NO 4
<211> LENGTH: 19
<212> TYPE: DNA
<213> ORGANISM: Homo sapiens

<400> SEQUENCE: 4
ttctagttgc agcgatgag                                                  19

<210> SEQ ID NO 5
<211> LENGTH: 19
<212> TYPE: DNA
<213> ORGANISM: Homo sapiens

<400> SEQUENCE: 5
catgcttagg attaggtgg                                                  19

<210> SEQ ID NO 6
<211> LENGTH: 10
<212> TYPE: PRT
<213> ORGANISM: Artificial Sequence
<220> FEATURE:
<223> OTHER INFORMATION: Synthetic control peptide

<400> SEQUENCE: 6

Ala Leu Trp Gly Gln Asp Val Thr Ser Val
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Synthetic Control Peptide

<400> SEQUENCE: 7

His Leu Phe Gly Tyr Ser Trp Tyr Lys
1               5